(12) United States Patent
Miller et al.

(10) Patent No.: US 11,279,946 B2
(45) Date of Patent: *Mar. 22, 2022

(54) BP005 TOXIN GENE AND METHODS FOR ITS USE

(71) Applicant: BASF Agricultural Solutions Seed US LLC, Florham Park, NJ (US)

(72) Inventors: Gabriel Miller, Morrisville, NC (US); Ethan Dunn, Durham, NC (US); James Doroghazi, Whippany, NJ (US); Duane Lehtinen, Morrisville, NC (US); Laura Schouten, Morrisville, NC (US); Andrew Debrecht, Morrisville, NC (US); Jonathan Giebel, Whippany, NJ (US); Daniel Vaknin, Morrisville, NC (US); Xunhai Zheng, Morrisville, NC (US); Kathleen Pitcher, Morrisville, NC (US)

(73) Assignee: BASF ARGICULTURAL SOLUTIONS SEED US LLC, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/478,236

(22) PCT Filed: Jan. 18, 2018

(86) PCT No.: PCT/US2018/014182
§ 371 (c)(1),
(2) Date: Jul. 16, 2019

(87) PCT Pub. No.: WO2018/136604
PCT Pub. Date: Jul. 26, 2018

(65) Prior Publication Data
US 2020/0123564 A1 Apr. 23, 2020

Related U.S. Application Data

(60) Provisional application No. 62/447,592, filed on Jan. 18, 2017.

(51) Int. Cl.
*C12N 15/82* (2006.01)
*A01N 63/22* (2020.01)
*C07K 14/32* (2006.01)

(52) U.S. Cl.
CPC ......... *C12N 15/8286* (2013.01); *A01N 63/22* (2020.01); *C07K 14/32* (2013.01)

(58) Field of Classification Search
None
See application file for complete search history.

(56) References Cited

U.S. PATENT DOCUMENTS 8,802,932 B2 * 8/2014 Altier ..................... C07K 14/37
800/301

FOREIGN PATENT DOCUMENTS

| CA | 2953903 A1 | 1/2016 |
| WO | 2010099365 A2 | 9/2010 |
| WO | 2015048332 A2 | 4/2015 |

OTHER PUBLICATIONS

Manns et al (2012, Appl. Environ. Microbiol. 78:2543-2552).*
Dodson et al (2008, Gen Bank Accession No. EDZ49333.1).*
Argolo-Filho et al, 2014, Insects 5:62-91.*
Guo et al, 2004, Proc. Natl. Acad. Sci. USA 101: 9205-9210.*
International Search Report received from corresponding PCT/US2018/014182, dated Jun. 5, 2018.
UniProt Accession No. A0A150BXA8, Last modified Jun. 1, 2016.
Database EMBL [Online] Dec. 23, 2010 (Dec. 23, 2010), "Bacillus thuringiensis antifungal protein (afn1) gene, complete cds.", retrieved from EBI accession No. EM_STD:FJ577896 Database accession No. FJ577896.
Database UniProt [Online] Nov. 2, 2016 (Nov. 2, 2016), "SubName: Full=Stress protein {ECO:0000313|EMBL:AHX21772.1};", retrieved from EBI accession No. UNIPROT:A0A023PEJ0 Database accession No. A0A023PEJ0.

* cited by examiner

Primary Examiner — Anne Kubelik
(74) Attorney, Agent, or Firm — Arent Fox LLP

(57) ABSTRACT

Compositions and methods for conferring pesticidal activity to bacteria, plants, plant cells, tissues and seeds are provided. Compositions comprising a coding sequence for a toxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated toxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in any of SEQ ID NO:1-40, 42, 43, 45-48, 50, 51, 52, 54, 56, 58-64, 66, or 67, or the nucleotide sequence set forth in any of SEQ ID NO:69-106, as well as variants and fragments thereof.

36 Claims, No Drawings
Specification includes a Sequence Listing.

SEQUENCE LISTING

```
<160> NUMBER OF SEQ ID NOS: 106

<210> SEQ ID NO 1
<211> LENGTH: 180
<212> TYPE: PRT
<213> ORGANISM: Bacillus cereus

<400> SEQUENCE: 1

Met Lys Lys Met Lys Lys Leu Val Asn Ile Ala Leu Ala Gly Thr Ile
1               5                   10                  15

Gly Leu Gly Gly Leu Gly Ala Phe Ala Pro Thr Asp Ala Ser Ala Ala
            20                  25                  30

Glu Val Ser Pro Ala Lys Thr Asn Ile Pro Thr Asn Leu Ser Thr Glu
        35                  40                  45

Leu Pro Thr Asn Phe Val Glu Ser Lys Leu Pro Asn Ala Ala Lys Ala
    50                  55                  60

Ser Ala Asn Leu Asp Val Ser Ile Asp Val Leu Gly Ile Ala Asn Leu
65                  70                  75                  80

Ile Arg Asn Ala Ile Asn Ser Gln Thr Asn Arg Ser Gly Phe Val Lys
                85                  90                  95

Gly Val Met Glu Ser Thr Phe Tyr Ser Ala Gly Gln Arg Tyr Asn Val
            100                 105                 110

Met Val Phe Asn Leu Asn Gln Asn Tyr Glu Asp Arg Phe Asn Gly Val
        115                 120                 125

Lys Phe Phe Gly Thr Thr Val Tyr Asp Gly Ile Thr Phe Gly Ile Trp
    130                 135                 140

Val Phe Glu Asp Gly Glu Phe Thr Asn Lys Gly Asp Gly Gly Trp Ile
145                 150                 155                 160

Asn Trp Ala Phe Arg Gly Trp Phe Asp Arg Asp Gly Gly His Val Lys
                165                 170                 175

Phe Tyr Arg Pro
            180

```
<210> SEQ ID NO 2
<211> LENGTH: 120
<212> TYPE: PRT
<213> ORGANISM: Artificial
<220> FEATURE:
<223> OTHER INFORMATION: bp005trun1

<400> SEQUENCE: 2

Met Ala Lys Ala Ser Ala Asn Leu Asp Val Ser Ile Asp Val Leu Gly
1               5                   10                  15

Ile Ala Asn Leu Ile Arg Asn Ala Ile Asn Ser Gln Thr Asn Arg Ser
            20                  25                  30

Gly Phe Val Lys Gly Val Met Glu Ser Thr Phe Tyr Ser Ala Gly Gln
        35                  40                  45

Arg Tyr Asn Val Met Val Phe Asn Leu Asn Gln Asn Tyr Glu Asp Arg
    50                  55                  60

Phe Asn Gly Val Lys Phe Gly Thr Thr Val Tyr Asp Gly Ile Thr
65                  70                  75                  80

Phe Gly Ile Trp Val Phe Glu Asp Gly Glu Phe Thr Asn Lys Gly Asp
                85                  90                  95

Gly Gly Trp Ile Asn Trp Ala Phe Arg Gly Trp Phe Asp Arg Asp Gly
            100                 105                 110

Gly His Val Lys Phe Tyr Arg Pro
        115                 120

<210> SEQ ID NO 3
<211> LENGTH: 117
<212> TYPE: PRT
<213> ORGANISM: Artificial
<220> FEATURE:
<223> OTHER INFORMATION: bp005v04

<400> SEQUENCE: 3

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Met Val Phe Asn Leu Asn Gln Asn Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 4
<211> LENGTH: 98
<212> TYPE: PRT
<213> ORGANISM: Artificial
<220> FEATURE:
<223> OTHER INFORMATION: bp005v06
```

```
<400> SEQUENCE: 4

Met Ala Ile Asn Ser Gln Thr Asn Arg Ser Gly Phe Val Lys Gly Val
1               5                   10                  15

Met Glu Ser Thr Phe Tyr Ser Ala Gly Gln Arg Tyr Asn Val Met Val
            20                  25                  30

Phe Asn Leu Asn Gln Asn Tyr Glu Asp Arg Phe Asn Gly Val Lys Phe
        35                  40                  45

Phe Gly Thr Thr Val Tyr Asp Gly Ile Thr Phe Gly Ile Trp Val Phe
    50                  55                  60

Glu Asp Gly Glu Phe Thr Asn Lys Gly Asp Gly Gly Trp Ile Asn Trp
65                  70                  75                  80

Ala Phe Arg Gly Trp Phe Asp Arg Asp Gly Gly His Val Lys Phe Tyr
                85                  90                  95

Arg Pro

<210> SEQ ID NO 5
<211> LENGTH: 178
<212> TYPE: PRT
<213> ORGANISM: Bacillus cereus

<400> SEQUENCE: 5

Met Gly Lys Met Lys Lys Ala Thr Gly Leu Leu Thr Gly Met Leu Leu
1               5                   10                  15

Ala Ile Ser Gly Ile Cys Thr Val Gly Thr Ser Gln Ala Ser Ala Glu
            20                  25                  30

Val Thr Pro Ala Pro Thr Thr Asn Lys Asn Ile Ser Leu Pro Tyr Ser
        35                  40                  45

Pro Leu Asp Pro Ile Leu Asn Lys Glu Asn Ala Asn L

```
Lys Gly Val Met Glu Ser Thr Phe Tyr Ala Ala Gly Gln Arg Tyr Asn
            35                  40                  45

Val Met Val Phe Asn Leu Asn Gln Asn Tyr Ser Asp Gln Phe Asn Gly
 50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Gln Gly Asp Gly Gly Trp
                    85                  90                  95

Ile Asn Trp Ala Phe Arg Gly Trp Phe Glu Arg Asn Gly Gly His Val
                100                 105                 110

Lys Phe His Arg Pro
            115

<210> SEQ ID NO 7
<211> LENGTH: 153
<212> TYPE: PRT
<213> ORGANISM: Bacillus cereus

<400> SEQUENCE: 7

Met Ala Phe Ala Pro Lys Asp Ala Ser Ala Ala Glu Ile Pro Lys Ala
 1               5                  10                  15

Thr Ile Ser Thr Glu Pro Gln Leu Thr Asn Lys Val Glu Asn Glu Lys
                20                  25                  30

Ala Val Lys Ser Phe Gly Ala Asn Leu Asn Val Asn Leu Asp Val Leu
            35                  40                  45

Gly Ile Thr Asp Arg Ile Ile Gly Ala Ile Asn Ser Ser Ala Asn Arg
 50                  55                  60

Ala Gly Phe Val Lys Gly Val Lys Glu Thr Ala Phe Tyr Ser Ala Gly
 65                  70                  75                  80

Gln Gln Tyr Asn Val Met Val Phe Asn Leu Asn Gln Asn Tyr Glu Asp
                    85                  90                  95

Arg Phe Asn Gly Val Lys Phe Phe Gly Thr Thr Val Tyr Asp Gly Ile
                100                 105                 110

Thr Phe Gly Ile Trp Val Phe Glu Asp Gly Glu Phe Thr Asn Lys Gly
            115                 120                 125

Asp Gly Gly Trp Ile Asn Trp Ala Phe Arg Gly Trp Phe Asp Arg Asp
 130                 135                 140

Gly Gly His Val Lys Phe Tyr Arg Pro
145                 150

<210> SEQ ID NO 8
<211> LENGTH: 117
<212> TYPE: PRT
<213> ORGANISM: Bacillus cereus

<400> SEQUENCE: 8

Met Gly Ala Asn Leu Asn Val Asn Leu Asp Val Leu Gly Ile Thr Asp
 1               5                  10                  15

Arg Ile Ile Gly Ala Ile Asn Ser Ser Ala Asn Arg Ala

```
Trp Val Phe Glu Asp Gly Glu Phe Thr Asn Lys Gly Asp Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 9
<211> LENGTH: 117
<212> TYPE: PRT
<213> ORGANISM: Bacillus cytotoxicus

<400> SEQUENCE: 9

Met Ser Ala Asn Leu Asp Val Ser Ile Asp Val Leu Gly Ile Ala Asn
1               5                   10                  15

Met Ile Arg Asp Ala Ile Asn Thr Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45

Val Met Val Phe Asn Leu Asn Gln Asn Tyr Asp Asp Arg Phe Asn Gly
50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Gly Trp
                85                  90                  95

Ile Asn Trp Ala Phe Arg Gly Trp Phe Asp Arg Asn Gly Asn His Val
            100                 105                 110

Lys Phe His Arg Ala
        115

<210> SEQ ID NO 10
<211> LENGTH: 117
<212> TYPE: PRT
<213> ORGANISM: Bacillus cereus

<400> SEQUENCE: 10

Met Ser Ala Asn Leu Asp Val Ser Ile Asp Val Leu Gly Ile Ala Asn
1               5                   10                  15

Leu Ile Arg Lys Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Lys Asp Ile Asn Leu Asn Gln Asn Tyr Glu Asp Arg Phe Asn Gly
50                  55                  60

Val Lys Leu Phe Gly Thr Thr Val Tyr Asp Gly Ile Thr Phe Gly Ile
65                  70                  75                  80

Cys Ile Phe Asp Glu Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 11
<211> LENGTH: 117
<212> TYPE: PRT
<213> ORGANISM: Bacillus cytotoxicus
```

<400> SEQUENCE: 11

Met Ser Ala Asn Leu Asn Val Ser Ile Asp Val Leu Gly Ile Ala Asn
1               5                   10                  15

Met Ile Arg Asp Ala Ile Asn Thr Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Met Val Phe Asn Leu Asn Gln Asn Tyr Asp Asp Arg Phe Asn Gly
    50                  55                  60

Val Lys Phe Phe Gly Thr Thr Val Tyr Asn Gly Ile Thr Phe Gly Ile
65                  70                  75                  80

Trp Val Phe Glu Asp Gly Glu Phe Thr Asn Gln Gly Asp Gly Gly Trp
                85                  90                  95

Ile Asn Trp Ala Phe Arg Gly Trp Phe Asp Arg Asn Gly Asn His Val
            100                 105                 110

Lys Phe His Arg Pro
        115

<210> SEQ ID NO 12
<211> LENGTH: 117
<212> TYPE: PRT
<213> ORGANISM: Bacillus pumilus

<400> SEQUENCE: 12

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Ile Glu Ser Thr Phe Tyr Ser Ala Cys Gln Leu Tyr Asn
        35                  40                  45

Val Ile Val Phe Asn Leu Asn His Asn Tyr Glu Asp Arg Phe Asn Phe
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly His His Val
            100                 105                 110

Lys Phe Tyr Arg Pro
        115

<210> SEQ ID NO 13
<211> LENGTH: 117
<212> TYPE: PRT
<213> ORGANISM: Bacillus thuringiensis

<400> SEQUENCE: 13

Met Ser Ala Asn Leu Asp Val Ser Ile Asp Val Leu Gly Ile Ala Asn
1               5                   10                  15

Met Ile Arg Asp Ala Ile Asn Ala Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45

Val Met Val Phe Asn Leu Asn Gln Asn Tyr Asn Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Gly Trp
                85                  90                  95

Ile Asn Trp Ala Phe Arg Gly Trp Phe Asp Arg Asn Gly Asn His Val
            100                 105                 110

Lys Phe Tyr Arg Pro
        115

<210> SEQ ID NO 14
<211> LENGTH: 117
<212> TYPE: PRT
<213> ORGANISM: Bacillus cytotoxicus

<400> SEQUENCE: 14

Met Ser Ala Asn Leu Asp Val Ser Ile Asp Val Leu Gly Ile Ala Asn
1               5                   10                  15

Met Ile Arg Asn Ser Ile Asn Thr Gln Thr Asn Arg Ser Gly Phe Val
                20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Asn Asp Arg Phe Asn Gly
        50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Gly Trp
                85                  90                  95

Ile Asn Trp Ala Phe Arg Gly Trp Phe Asp Arg Asn Gly Asn His Val
            100                 105                 110

Lys Phe His Arg Gln
        115

<210> SEQ ID NO 15
<211> LENGTH: 117
<212> TYPE: PRT
<213> ORGANISM: Bacillus thuringiensis

<400> SEQUENCE: 15

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
                20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
        50                  55                  60

Val Lys Phe Leu Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Lys Met Ala Phe Arg Gly Arg Ile Asp Arg Asp Ala His Thr Val
            100                 105                 110

Lys Phe Tyr Arg Gln
        115

-continued

<210> SEQ ID NO 16
<211> LENGTH: 117
<212> TYPE: PRT
<213> ORGANISM: Bacillus thuringiensis

<400> SEQUENCE: 16

Met Ser Ala Asn Leu Asn Val Asn Val Asp Val Leu Gly Ile Ala Asn
1               5                   10                  15

Met Ile Arg Asp Ala Ile Asn Ala Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45

Val Met Val Phe Asn Leu Asn Gln Asn Tyr Gln Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Trp
                85                  90                  95

Ile Asn Trp Ala Phe Arg Gly Trp Phe Asp Arg Asn Gly Gly His Val
            100                 105                 110

Lys Phe Tyr Arg Gly
        115

<210> SEQ ID NO 17
<211> LENGTH: 117
<212> TYPE: PRT
<213> ORGANISM: Bacillus weihenstephanensis

<400> SEQUENCE: 17

Met Ser Ala Asn Leu Ser Val Asn Val Asp Val Leu Gly Ile Ala Asn
1               5                   10                  15

Met Val Arg Asp Ala Ile Asn Ala Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45

Val Met Val Phe Asn Leu Asn Gln Asn Tyr Asp Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Trp
                85                  90                  95

Ile Asn Trp Ala Phe Arg Gly Trp Phe Asp Arg Asn Gly Asn His Val
            100                 105                 110

Lys Phe His Arg Ala
        115

<210> SEQ ID NO 18
<211> LENGTH: 117
<212> TYPE: PRT
<213> ORGANISM: Bacillus thuringiensis

<400> SEQUENCE: 18

Met Ser Ala Asn Leu Asp Val Ser Ile Asp Val Leu Gly Ile Ala Asn
1               5                   10                  15

Met Ile Arg Asp Ala Ile Asn Ala Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45

Val Met Val Phe Asn Leu Asn Gln Asn Tyr Asp Asp Arg Phe Asn Gly
        50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Gln Gly Asp Gly Gly Trp
                    85                  90                  95

Ile Asn Trp Ala Phe Arg Gly Trp Phe Asp Arg Asn Gly Asn His Val
                100                 105                 110

Lys Phe His Arg Ala
            115

<210> SEQ ID NO 19
<211> LENGTH: 117
<212> TYPE: PRT
<213> ORGANISM: Bacillus cytotoxicus

<400> SEQUENCE: 19

Met Ser Ala Asn Leu Asn Val Ser Ile Asp Val Leu Gly Ile Ala Asn
 1                5                  10                  15

Met Ile Arg Asp Ala Ile Asn Thr Gln Thr Asn Arg Ser Gly Phe Val
                 20                  25                  30

Lys Gly Val Met Glu Ser Thr Phe Tyr Ser Ala Gly Gln Arg Tyr Asn
                 35                  40                  45

Val Met Val Phe Asn Leu Asn Gln Asn Tyr Asp Asp Arg Phe Asn Gly
        50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Gln Gly Asp Gly Gly Trp
                    85                  90                  95

Ile Asn Trp Ala Phe Arg Gly Trp Phe Asp Arg Asn Gly Asn His Val
                100                 105                 110

Lys Phe His Arg Pro
            115

<210> SEQ ID NO 20
<211> LENGTH: 117
<212> TYPE: PRT
<213> ORGANISM: Bacillus cytotoxicus

<400> SEQUENCE: 20

Met Ser Ala Asn Leu Asp Val Ser Ile Asp Val Leu Gly Ile Ala Asn
 1                5                  10                  15

Met Ile Arg Asn Ser Ile Asn Thr Gln Thr Asn Arg Ser Gly Phe Val
                 20                  25                  30

Lys Gly Val Met Glu Ser Thr Phe Tyr Ser Ala Gly Gln Arg Tyr Asn
                 35                  40                  45

Val Met Val Phe Asn Leu Asn Gln Asn Tyr Asn Asp Arg Phe Asn Gly
        50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Gln Gly Asp Gly Gly Trp
                    85                  90                  95

Ile Asn Trp Ala Phe Arg Gly Trp Phe Asp Arg Asn Gly Asn His Val
                100                 105                 110

Lys Phe His Arg Pro
            115

```
<210> SEQ ID NO 21
<211> LENGTH: 117
<212> TYPE: PRT
<213> ORGANISM: Bacillus thuringiensis

<400> SEQUENCE: 21

Met Ser Ala Asn Leu Asp Val Ser Ile Asp Val Leu Gly Ile Ala Asn
1               5                   10                  15

Met Ile Arg Asp Ala Ile Asn Ala Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45

Val Met Val Phe Asn Leu Asn Gln Asn Tyr Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 22
<211> LENGTH: 109
<212> TYPE: PRT
<213> ORGANISM: Bacillus weihenstephanensis

<400> SEQUENCE: 22

Met Asp Val Leu Gly Ile Ala Asn Met Ile Arg Asp Ala Ile Asn Thr
1               5                   10                  15

Gln Thr Asn Arg Ser Gly Phe Val Lys Gly Val Met Glu Ser Thr Phe
            20                  25                  30

Tyr Ala Ala Gly Gln Arg Tyr Asn Val Met Val Phe Asn Leu Asn Gln
        35                  40                  45

Asn Tyr Gln Asp Arg Phe Asn Gly Val Lys Phe Phe Gly Thr Thr Val
    50                  55                  60

Tyr Asp Gly Ile Thr Phe Gly Ile Trp Val Phe Glu Asp Gly Glu Phe
65                  70                  75                  80

Thr Asn Gln Gly Asp Gly Gly Trp Ile Asn Trp Ala Phe Arg Gly Trp
                85                  90                  95

Phe Asp Arg Asn Gly Gly His Val Lys Phe Tyr Arg Gly
            100                 105

<210> SEQ ID NO 23
<211> LENGTH: 117
<212> TYPE: PRT
<213> ORGANISM: Bacillus weihenstephanensis

<400> SEQUENCE: 23

Met Ser Ala Asn Leu Ser Val Asn Val Asp Val Leu Gly Ile Ala Asn
1               5                   10                  15

Met Ile Arg Asp Ala Ile Asn Thr Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45
```

```
Val Met Val Phe Asn Leu Asn Gln Asn Tyr Gln Asp Arg Phe Asn Gly
     50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Gln Gly Asp Gly Gly Trp
                 85                  90                  95

Ile Asn Trp Ala Phe Arg Gly Trp Phe Asp Arg Asn Gly Gly His Val
                100                 105                 110

Lys Phe Tyr Arg Gly
            115

<210> SEQ ID NO 24
<211> LENGTH: 122
<212> TYPE: PRT
<213> ORGANISM: Bacillus cereus

<400> SEQUENCE: 24

Met Asn Ala Asn Lys Val Asp Gly Gln Leu Asn Val Asn Ile Asp Val
 1               5                  10                  15

Leu Gly Ile Ala Asn Met Ile Arg Asp Ala Ile Asn Ala Gln Thr Asn
                20                  25                  30

Arg Ser Gly Phe Val

```
<210> SEQ ID NO 26
<211> LENGTH: 118
<212> TYPE: PRT
<213> ORGANISM: Bacillus thuringiensis

<400> SEQUENCE: 26

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Phe Ser Ala Gly Gln Arg Tyr Tyr
        35                  40                  45

Val Met Val Phe Asn Leu Asn Gln Asn Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Cys Glu Phe Lys Asn Lys Gly Asp Gly Gly Trp
                85                  90                  95

Tyr Asn Trp Ser Leu Arg Gly Trp Phe Asp Arg Asp Gly Gly His Val
            100                 105                 110

Ile Phe Tyr Arg Pro Leu
            115

<210> SEQ ID NO 27
<211> LENGTH: 117
<212> TYPE: PRT
<213> ORGANISM: Bacillus thuringiensis

<400> SEQUENCE: 27

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Tyr Val
            20                  25                  30

Ile Gly Glu Met Asp Ser Thr Ile Asn Thr Ala Gly Gln Arg Tyr Asn
        35                  40                  45

Val Met Val Phe Ile Leu Asn Gln Asn Tyr Glu Asp Arg Phe Asn Gly
    50                  55                  60

Val Asn Phe Phe Gly Thr Thr Val Tyr Asp Gly Phe Thr Phe Gly Ile
65                  70                  75                  80

Ser Ala Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 28
<211> LENGTH: 117
<212> TYPE: PRT
<213> ORGANISM: Bacillus thuringiensis

<400> SEQUENCE: 28

Met Arg Ala Asn Leu Asp Val Ser Ile Asp Val Leu Gly Ile Ala Asn
1               5                   10                  15

Leu Ile Arg Asn Ala Ile Asn Ser His Thr Asn Arg Ser Gly Phe Val
            20                  25                  30

Asn Gly Val Met Glu Ser Thr Phe Tyr Ser Ala Gly Gln Arg Tyr Asn
        35                  40                  45
```

Val Ile Val Leu Asn Leu Asn His Ile Tyr Glu Asp Arg Phe Asn Cys
 50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Ser Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
            115

<210> SEQ ID NO 29
<211> LENGTH: 117
<212> TYPE: PRT
<213> ORGANISM: Bacillus thuringiensis

<400> SEQUENCE: 29

Met Ser Glu Asn Leu Asp Gly Ser Ile Asp Val Leu Cys Phe Ala Asn
1               5                   10                  15

Leu Ile Arg Asn Val Phe Asn Ser His Thr Asn Arg Ser Gly Phe Val
                20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
 50                  55                  60

Val Lys Phe Ile Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
            115

<210> SEQ ID NO 30
<211> LENGTH: 117
<212> TYPE: PRT
<213> ORGANISM: Bacillus cereus

<400> SEQUENCE: 30

Met Gly Ala Asn Leu Asn Val Asn Leu Asp Val Leu Gly Ile Thr Asp
1               5                   10                  15

Arg Ile Ile Gly Ala Ile Asn Ser Ser Ala Asn Arg Ala Gly Phe Val
                20                  25                  30

Lys Gly Val Lys Glu Thr Ala Phe Tyr Ser Ala Gly Gln Gln Tyr Asn
            35                  40                  45

Val Met Val Phe Asn Leu Asn Gln Asn Tyr Glu Asp Arg Phe Asn Gly
 50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
            115

-continued

<210> SEQ ID NO 31
<211> LENGTH: 117
<212> TYPE: PRT
<213> ORGANISM: Bacillus thuringiensis

<400> SEQUENCE: 31

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Met Val Phe Asn Leu Asn Gln Asn Tyr Glu Asp Arg Phe Asn Gly
    50                  55                  60

Ile Lys Phe Phe Gly Thr Thr Val Tyr Asp Gly Ile Thr Phe Gly Ile
65                  70                  75                  80

Trp Val Phe Glu Asp Val Val Phe Thr Asn Lys Gly Asp Gly Gly Trp
                85                  90                  95

Ile Asn Trp Ser Phe Arg Cys Leu Phe Asp Leu Asp Gly His Val
            100                 105                 110

Lys Phe Tyr Arg Pro
        115

<210> SEQ ID NO 32
<211> LENGTH: 117
<212> TYPE: PRT
<213> ORGANISM: Bacillus thuringiensis

<400> SEQUENCE: 32

Met Ser Ala Asn Leu Asn Val Ser Ile Asp Val Leu Gly Ile Ala Asn
1               5                   10                  15

Met Ile Lys Asp Ala Ile Asn Ala Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45

Val Met Val Phe Asn Leu Asn Gln Asn Tyr Asp Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Gly Trp
                85                  90                  95

Ile Asn Trp Ala Phe Arg Gly Trp Phe Asp Arg Asn Gly Asn His Val
            100                 105                 110

Lys Phe His Arg Ala
        115

<210> SEQ ID NO 33
<211> LENGTH: 117
<212> TYPE: PRT
<213> ORGANISM: Bacillus thuringiensis

<400> SEQUENCE: 33

Met Ser Ala Asn Leu Asn Val Ser Ile Asp Val Leu Gly Ile Ala Asn
1               5                   10                  15

Met Ile Lys Asp Ala Ile Asn Ala Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45

Val Met Val Phe Asn Leu Asn Gln Tyr Tyr Asp Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Gly Trp
                85                  90                  95

Ile Asn Trp Ala Phe Arg Gly Trp Phe Asp Arg Asn Gly Asn His Val
                100                 105                 110

Lys Phe His Arg Ala
        115

<210> SEQ ID NO 34
<211> LENGTH: 117
<212> TYPE: PRT
<213> ORGANISM: Bacillus cytotoxicus

<400> SEQUENCE: 34

Met Ser Ala Asn Leu Asn Val Ser Ile Asp Val Leu Gly Ile Ala Asn
1               5                   10                  15

Met Ile Lys Asn Ser Ile Asn Thr Gln Thr Asn Arg Ser Gly Phe Val
                20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Asn Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Gly Trp
                85                  90                  95

Ile Asn Trp Ala Phe Arg Gly Trp Phe Asp Arg Asn Gly Asn His Val
                100                 105                 110

Lys Phe His Arg Pro
        115

<210> SEQ ID NO 35
<211> LENGTH: 117
<212> TYPE: PRT
<213> ORGANISM: Bacillus thuringiensis

<400> SEQUENCE: 35

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Asn Val
                20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
    50                  55                  60

Gly Ile Phe Phe Gly Thr Thr Val Phe Asp Gly Phe Thr Phe Gly Ile
65                  70                  75                  80

Trp Val Phe Glu Val Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
        115

```
<210> SEQ ID NO 36
<211> LENGTH: 117
<212> TYPE: PRT
<213> ORGANISM: Bacillus thuringiensis

<400> SEQUENCE: 36

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Met Val Phe Asn Leu Asn Gln Asn Tyr Glu Asp Arg Phe Asn Gly
    50                  55                  60

Ile Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Glu Gly Gly Trp
                85                  90                  95

Ile Asn Trp Glu Phe Arg Val Trp Leu Asp Arg Asp Gly Gly Leu Val
            100                 105                 110

Lys Phe Tyr Arg Pro
        115

<210> SEQ ID NO 37
<211> LENGTH: 117
<212> TYPE: PRT
<213> ORGANISM: Bacillus thuringiensis

<400> SEQUENCE: 37

Met Ser Ala Asn Leu Ser Val Asn Val Asp Val Leu Gly Ile Ala Asn
1               5                   10                  15

Met Ile Arg Asp Ala Ile Asn Thr Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45

Val Met Val Phe Asn Leu Asn Gln Asn Tyr Gln Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Asp Gly Gly Trp
                85                  90                  95

Ile Asn Trp Ala Phe Arg Gly Trp Phe Asp Arg Asp Gly Gly Tyr Val
            100                 105                 110

Lys Phe Tyr Arg Gly
        115

<210> SEQ ID NO 38
<211> LENGTH: 117
<212> TYPE: PRT
<213> ORGANISM: Bacillus pumilus

<400> SEQUENCE: 38

Met Ser Ala Asn Leu Asn Val Ser Ile Asp Val Leu Gly Ile Ala Asn
1               5                   10                  15

Met Ile Lys Asp Ala Ile Asn Ala Gln Thr Asn Arg Ser Gly Phe Val
            20                  25                  30

Lys Gly Val Met Glu Ser Thr Phe Tyr Ala Ala Gly Gln Arg Tyr Asn
        35                  40                  45
```

Val Met Val Phe Asn Leu Asn Gln Asn Tyr Asp Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Gln Gly Asp Gly Gly Trp
                85                  90                  95

Ile Asn Trp Ala Phe Arg Gly Trp Phe Asp Arg Asn Gly Asn His Val
                100                 105                 110

Lys Phe His Arg Ala
        115

<210> SEQ ID NO 39
<211> LENGTH: 117
<212> TYPE: PRT
<213> ORGANISM: Artificial
<220> FEATURE:
<223> OTHER INFORMATION: bp005 mutant

<400> SEQUENCE: 39

Met Ser Ala Asn Leu Asp Val Ser Ile Asp Val Leu Gly Ile Gly Asn
1               5                   10                  15

Leu Ile Arg Asn Ala Ile Asn Ser Gln Thr Asn Arg Ser Gly Phe Val
                20                  25                  30

Lys Gly Val Met Glu Ser Thr Phe Tyr Ser Ala Gly Gln Arg Tyr Asn
                35                  40                  45

Val Met Val Phe Asn Leu Asn Gln Asn Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
        115

<210> SEQ ID NO 40
<211> LENGTH: 117
<212> TYPE: PRT
<213> ORGANISM: Artificial
<220> FEATURE:
<223> OTHER INFORMATION: bp005 mutant

<400> SEQUENCE: 40

Met Ser Ala Asn Leu Ser Val Ser Ile Asp Val Leu Gly Ile Ala Asn
1               5                   10                  15

Leu Ile Arg Asn Ala Ile Asn Ser Gln Thr Asn Arg Ser Gly Phe Val
                20                  25                  30

Lys Gly Val Met Glu Ser Thr Phe Tyr Ser Ala Gly Gln Arg Tyr Asn
                35                  40                  45

Val Met Val Phe Asn Leu Asn Gln Asn Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

```
Ile Asn Trp Ala Phe Arg Gly Trp Phe Asp Arg Asp Gly Gly His Val
            100                 105                 110

Lys Phe Tyr Arg Pro
        115

<210> SEQ ID NO 41
<211> LENGTH: 117
<212> TYPE: PRT
<213> ORGANISM: Artificial
<220> FEATURE:
<223> OTHER INFORMATION: bp005 mutant

<400> SEQUENCE: 41

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
        50                  55                  60

Val Lys Phe Phe Gly Thr Thr Val Tyr His Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 42
<211> LENGTH: 117
<212> TYPE: PRT
<213> ORGANISM: Artificial
<220> FEATURE:
<223> OTHER INFORMATION: bp005 mutant

<400> SEQUENCE: 42

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
        50                  55                  60

Val Lys Phe Phe Gly Thr Thr Val Tyr Asp Gly Ile Thr Phe Gly Ile
65                  70                  75                  80

Trp Val Phe Glu Ser Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 43
<211> LENGTH: 117
<212> TYPE: PRT
<213> ORGANISM: Artificial
```

```
<220> FEATURE:
<223> OTHER INFORMATION: bp005 mutant

<400> SEQUENCE: 43

Met Ser Ala Asn Phe Asp Val Ser Ile Asp Val Leu Gly Ile Ala Asn
1               5                   10                  15

Leu Ile Arg Asn Ala Ile Asn Ser Gln Thr Asn Arg Pro Gly Phe Val
            20                  25                  30

Lys Gly Met Met Glu Ser Thr Phe Tyr Ser Ala Gly Gln Lys Tyr Asn
        35                  40                  45

Val Met Val Phe Asn Leu Ala Gln Asn Tyr Glu Asp His Phe Arg Gly
50                      55                  60

Val Lys Phe Phe Gly Thr Thr Val Leu Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Asp Asn Trp Ala Phe Arg Gly Trp Phe Asp Arg Asp Gly Gly Tyr Val
                100                 105                 110

Lys Phe Tyr Arg Pro
            115

<210> SEQ ID NO 44
<211> LENGTH: 117
<212> TYPE: PRT
<213> ORGANISM: Artificial
<220> FEATURE:
<223> OTHER INFORMATION: bp005 mutant

<400> SEQUENCE: 44

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Met Val Phe Asn Leu Asn Gln Asn Tyr Glu Asp Arg Phe Asn Gly
50                      55                  60

Val Lys Phe Phe Gly Thr Thr Val Tyr Asp Gly Ile Thr Phe Gly Ile
65                  70                  75                  80

Trp Val Phe Glu Asp Gly Gln Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
            115

<210> SEQ ID NO 45
<211> LENGTH: 117
<212> TYPE: PRT
<213> ORGANISM: Artificial
<220> FEATURE:
<223> OTHER INFORMATION: bp005 mutant

<400> SEQUENCE: 45

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30
```

-continued

Lys Gly Val Met Glu Ser Thr Phe Tyr Ser Ala Gly Gln Arg Tyr Asn
             35                  40                  45

Val Met Val Phe Asn Leu Asn Gln Asn Tyr Glu Asp Arg Phe Asn Gly
 50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Lys Gly Asp Gly Gly Trp
                 85                  90                  95

Ile Asn Trp Ala Phe Arg Gly Trp Phe Asp Arg Asp Gly Gly Tyr Val
                100                 105                 110

Lys Phe Tyr Arg Pro
        115

<210> SEQ ID NO 46
<211> LENGTH: 117
<212> TYPE: PRT
<213> ORGANISM: Artificial
<220> FEATURE:
<223> OTHER INFORMATION: bp005 mutant

<400> SEQUENCE: 46

Met Ser Ala Asn Leu Asp Val Ser Ile Asp Val Leu Gly Ile Ala Asn
 1               5                  10                  15

Leu Ile Arg Asn Ala Ile Asn Ser Gln Thr Asn Arg Ser Gly Phe Val
                 20                  25                  30

Lys Gly Val Met Glu Ser Thr Phe Tyr Ser Ala Gly Gln Arg Tyr Asn
             35                  40                  45

Val Met Val Phe Asn Leu Asn Gln Asn Tyr Glu Asp Arg Phe Asn Gly
 50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Lys Gly Asp Gly Gly Trp
                 85                  90                  95

Asp Asn Trp Ala Phe Arg Gly Trp Phe Asp Arg Asp Gly Gly His Val
                100                 105                 110

Lys Phe Tyr Arg Pro
        115

<210> SEQ ID NO 47
<211> LENGTH: 117
<212> TYPE: PRT
<213> ORGANISM: Artificial
<220> FEATURE:
<223> OTHER INFORMATION: bp005 mutant

<400> SEQUENCE: 47

Met Ser Ala Asn Leu Asp Val Ser Ile Asp Val Leu Gly Ile Ala Asn
 1               5                  10                  15

Leu Ile Arg Asn Ala Ile Asn Ser Gln Thr Asn Arg Ser Gly Phe Val
                 20                  25                  30

Lys Gly Val Met Glu Ser Thr Phe Tyr Ser Ala Gly Gln Arg Tyr Asn
             35                  40                  45

Val Met Val Phe Asn Leu Asn Gln Asn Tyr Glu Asp Arg Phe Asn Gly
 50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Lys Gly Asp Gly Gly Trp
                 85                  90                  95

Ile Asn Trp Ala Phe Arg Gly Trp Phe Asp Arg Asp Gly Gly His Val
            100                 105                 110

Glu Phe Tyr Arg Pro
        115

<210> SEQ ID NO 48
<211> LENGTH: 117
<212> TYPE: PRT
<213> ORGANISM: Artificial
<220> FEATURE:
<223> OTHER INFORMATION: bp005 mutant

<400> SEQUENCE: 48

Met Ser Ala Asn Phe Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Met Val Phe Asn Leu Asn Gln Asn Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 49
<211> LENGTH: 117
<212> TYPE: PRT
<213> ORGANISM: Artificial
<220> FEATURE:
<223> OTHER INFORMATION: bp005 mutant

<400> SEQUENCE: 49

Met Ser Ala Asn Leu Asp Val Ser Ile Asp Val Leu Gly Ile Ala Asn
1               5                   10                  15

Leu Ile Arg Asn Ala Ile Lys Ser Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Met Val Phe Asn Leu Asn Gln Asn Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 50
<211> LENGTH: 117
<212> TYPE: PRT
<213> ORGANISM: Artificial

```
<220> FEATURE:
<223> OTHER INFORMATION: bp005 mutant

<400> SEQUENCE: 50

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Met Val Phe Asn Leu Ala Gln Asn Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
            115

<210> SEQ ID NO 51
<211> LENGTH: 117
<212> TYPE: PRT
<213> ORGANISM: Artificial
<220> FEATURE:
<223> OTHER INFORMATION: bp005 mutant

<400> SEQUENCE: 51

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
        35                  40                  45

Val Met Val Phe Asn Leu Asn Gln Gly Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
            115

<210> SEQ ID NO 52
<211> LENGTH: 117
<212> TYPE: PRT
<213> ORGANISM: Artificial
<220> FEATURE:
<223> OTHER INFORMATION: bp005 mutant

<400> SEQUENCE: 52

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30
```

Lys Gly Val Met Glu Ser Thr Phe Tyr Ser Ala Gly Gln Arg Tyr Asn
                35                  40                  45

Val Met Val Phe Asn Leu Asn Gln Asn Tyr Glu Asp Arg Phe Arg Gly
 50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
            115

<210> SEQ ID NO 53
<211> LENGTH: 117
<212> TYPE: PRT
<213> ORGANISM: Artificial
<220> FEATURE:
<223> OTHER INFORMATION: bp005 mutant

<400> SEQUENCE: 53

Met Ser Ala Asn Leu Ser Val Ser Ile Asp Val Leu Gly Ile Gly Asn
 1               5                   10                  15

Leu Ile Arg Asn Ala Ile Asn Ser Gln Thr Asn Arg Ser Gly Phe Val
                20                  25                  30

Lys Gly Cys Met Glu Ser Thr Phe Tyr Ser Ala Gly Gln Arg Tyr Asn
                35                  40                  45

Val Met Val Phe Asn Leu Asn Gln Gly Tyr Glu Asp Arg Phe Asn Gly
 50                  55                  60

Val Lys Phe Phe Gly Thr Thr Asn Tyr His Gly Ile Thr Phe Gly Ile
 65                  70                  75                  80

Trp Val Phe Glu Ser Gly Gln Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
            115

<210> SEQ ID NO 54
<211> LENGTH: 117
<212> TYPE: PRT
<213> ORGANISM: Artificial
<220> FEATURE:
<223> OTHER INFORMATION: bp005 mutant

<400> SEQUENCE: 54

Met Ser Ala Asn Leu Asp Val Ser Ile Asp Val Leu Gly Ile Ala Asn
 1               5                   10                  15

Leu Ile Ala Asn Ala Ile Lys Ser Gln Gln Asn Arg Ser Gly Phe Val
                20                  25                  30

Lys Gly Val Met Glu Ser Thr Phe Tyr Ser Ala Gly Gln Arg Tyr Asn
                35                  40                  45

Val Met Val Phe Asn Leu Asn Gln Asn Tyr Glu Asp Arg Phe Asn Gly
 50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Lys Gly Asp Gly Gly Trp
                85                  90                  95

-continued

Ile Asn Trp Ala Phe Arg Gly Trp Phe Asp Arg Asp Gly Gly His Val
                100                 105                 110

Glu Phe Tyr Arg Pro
        115

<210> SEQ ID NO 55
<211> LENGTH: 117
<212> TYPE: PRT
<213> ORGANISM: Artificial
<220> FEATURE:
<223> OTHER INFORMATION: bp005 mutant

<400> SEQUENCE: 55

Met Ser Ala Asn Phe Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
                20                  25                  30

Lys Gly Met Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
        50                  55                  60

Val Lys Phe Phe Gly Thr Thr Val Leu Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Asp Asn Trp Ala Phe Arg Gly Trp Phe Asp Arg Asp Gly Gly His Val
                100                 105                 110

Lys Phe Tyr Arg Pro
        115

<210> SEQ ID NO 56
<211> LENGTH: 117
<212> TYPE: PRT
<213> ORGANISM: Artificial
<220> FEATURE:
<223> OTHER INFORMATION: bp005 mutant

<400> SEQUENCE: 56

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Pro Gly Phe Val
                20                  25                  30

Lys Gly Val Met Glu Ser Thr Phe Tyr Ser Ala Gly Gln Lys Tyr Asn
            35                  40                  45

Val Met Val Phe Asn Leu Ala Gln Asn Tyr Glu Asp Arg Phe Asn Gly
        50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly Tyr Val
                100                 105                 110

Lys Phe Tyr Arg Pro
        115

<210> SEQ ID NO 57
<211> LENGTH: 117
<212> TYPE: PRT
<213> ORGANISM: Artificial

```
<220> FEATURE:
<223> OTHER INFORMATION: bp005 mutant

<400> SEQUENCE: 57

Met Ser Ala Asn Leu Ser Val Ser Ile Asp Val Leu Gly Ile Gly Asn
1               5                   10                  15

Leu Ile Arg Asn Ala Ile Asn Ser Gln Thr Asn Arg Ser Gly Phe Val
                20                  25                  30

Lys Gly Cys Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
        50                  55                  60

Val Lys Phe Phe Gly Thr Thr Val Tyr His Gly Ile Thr Phe Gly Ile
65                  70                  75                  80

Trp Val Phe Glu Ser Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
            115

<210> SEQ ID NO 58
<211> LENGTH: 117
<212> TYPE: PRT
<213> ORGANISM: Artificial
<220> FEATURE:
<223> OTHER INFORMATION: bp005 mutant

<400> SEQUENCE: 58

Met Ser Ala Asn Leu Asp Val Ser Ile Asp Val Leu Gly Ile Ala Asn
1               5                   10                  15

Leu Ile Ala Asn Ala Ile Asn Ser Gln Thr Asn Arg Ser Gly Phe Val
                20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
        50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
            115

<210> SEQ ID NO 59
<211> LENGTH: 117
<212> TYPE: PRT
<213> ORGANISM: Artificial
<220> FEATURE:
<223> OTHER INFORMATION: bp005 mutant

<400> SEQUENCE: 59

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
                20                  25                  30
```

```
Lys Gly Val Met Glu Ser Thr Phe Tyr Ser Ala Gly Gln Lys Tyr Asn
            35                  40                  45

Val Met Val Phe Asn Leu Asn Gln Asn Tyr Glu Asp Arg Phe Asn Gly
 50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Lys Gly Asp Gly Gly Trp
                 85                  90                  95

Ile Asn Trp Ala Phe Arg Gly Trp Phe Asp Arg Asp Gly Gly His Val
                100                 105                 110

Lys Phe Tyr Arg Pro
        115

<210> SEQ ID NO 60
<211> LENGTH: 117
<212> TYPE: PRT
<213> ORGANISM: Artificial
<220> FEATURE:
<223> OTHER INFORMATION: bp005 mutant

<400> SEQUENCE: 60

Met Ser Ala Asn Leu Asp Val Ser Ile Asp Val Leu Gly Ile Ala Asn
 1               5                  10                  15

Leu Ile Arg Asn Ala Ile Asn Ser Gln Thr Asn Arg Ser Gly Phe Val
                 20                  25                  30

Lys Gly Val Met Glu Ser Thr Phe Tyr Ser Ala Gly Gln Arg Tyr Asn
            35                  40                  45

Val Met Val Phe Asn Leu Gln Asn Tyr Glu Asp His Phe Asn Gly
 50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Lys Gly Asp Gly Gly Trp
                 85                  90                  95

Ile Asn Trp Ala Phe Arg Gly Trp Phe Asp Arg Asp Gly Gly His Val
                100                 105                 110

Lys Phe Tyr Arg Pro
        115

<210> SEQ ID NO 61
<211> LENGTH: 117
<212> TYPE: PRT
<213> ORGANISM: Artificial
<220> FEATURE:
<223> OTHER INFORMATION: bp005 mutant

<400> SEQUENCE: 61

Met Ser Ala Asn Leu Asp Val Ser Ile Asp Val Leu Gly Ile Ala Asn
 1               5                  10                  15

Leu Ile Arg Asn Ala Ile Asn Ser Gln Thr Asn Arg Pro Gly Phe Val
                 20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
 50                  55                  60

Val Lys Phe Phe Gly Thr Thr Val Tyr Asp Gly Ile Thr Phe Gly Ile
 65                  70                  75                  80

Trp Val Phe Glu Asp Gly Glu Phe Thr Asn Lys Gly Asp Gly Gly Trp
                 85                  90                  95
```

```
Ile Asn Trp Ala Phe Arg Gly Trp Phe Asp Arg Asp Gly Gly His Val
                100                 105                 110

Lys Phe Tyr Arg Pro
        115

<210> SEQ ID NO 62
<211> LENGTH: 117
<212> TYPE: PRT
<213> ORGANISM: Artificial
<220> FEATURE:
<223> OTHER INFORMATION: bp005 mutant

<400> SEQUENCE: 62

Met Ser Ala Asn Leu Asp Val Ser Ile Asp Val Leu Gly Ile Ala Asn
1               5                   10                  15

Leu Ile Arg Asn Ala Ile Asn Ser Gln Gln Asn Arg Ser Gly Phe Val
                20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
        50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
        115

<210> SEQ ID NO 63
<211> LENGTH: 117
<212> TYPE: PRT
<213> ORGANISM: Artificial
<220> FEATURE:
<223> OTHER INFORMATION: bp005 mutant

<400> SEQUENCE: 63

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
                20                  25                  30

Lys Gly Val Met Glu Ser Thr Phe Tyr Ser Ala Gly Gln Arg Tyr Asn
            35                  40                  45

Val Met Val Phe Asn Leu Asn Gln Gly Tyr Glu Asp Arg Phe Asn Gly
        50                  55                  60

Val Lys Phe Phe Gly Thr Thr Asn Tyr Asp Gly Ile Thr Phe Gly Ile
65                  70                  75                  80

Trp Val Phe Glu Asp Gly Gln Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
        115

<210> SEQ ID NO 64
<211> LENGTH: 117
<212> TYPE: PRT
<213> ORGANISM: Artificial
```

```
<220> FEATURE:
<223> OTHER INFORMATION: bp005 mutant

<400> SEQUENCE: 64

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Cys Met Glu Ser Thr Phe Tyr Ser Ala Gly Gln Arg Tyr Asn
        35                  40                  45

Val Met Val Phe Asn Leu Asn Gln Asn Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
        115

<210> SEQ ID NO 65
<211> LENGTH: 117
<212> TYPE: PRT
<213> ORGANISM: Artificial
<220> FEATURE:
<223> OTHER INFORMATION: bp005 mutant

<400> SEQUENCE: 65

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30

Lys Gly Met Met Glu Ser Thr Phe Tyr Ser Ala Gly Gln Arg Tyr Asn
        35                  40                  45

Val Met Val Phe Asn Leu Asn Gln Asn Tyr Glu Asp Arg Phe Asn Gly
    50                  55                  60

Val Lys Phe Phe Gly Thr Thr Val Tyr Asp Gly Ile Thr Phe Gly Ile
65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
                100                 105                 110

Lys Phe Tyr Arg Pro
        115

<210> SEQ ID NO 66
<211> LENGTH: 117
<212> TYPE: PRT
<213> ORGANISM: Artificial
<220> FEATURE:
<223> OTHER INFORMATION: bp005 mutant

<400> SEQUENCE: 66

Met Ser Ala Asn Leu Asp Val Ser Ile Asp Val Leu Gly Ile Ala Asn
1               5                   10                  15

Leu Ile Arg Asn Ala Ile Asn Ser Gln Thr Asn Arg Ser Gly Phe Val
            20                  25                  30
```

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
 50                  55                  60

Val Lys Phe Phe Gly Thr Thr Asn Tyr Asp Gly Ile Thr Phe Gly Ile
 65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 67
<211> LENGTH: 117
<212> TYPE: PRT
<213> ORGANISM: Artificial
<220> FEATURE:
<223> OTHER INFORMATION: bp005 mutant

<400> SEQUENCE: 67

Met Ser Ala Asn Leu Asp Val Ser Ile Asp Val Leu Gly Ile Ala Asn
 1               5                  10                  15

Leu Ile Arg Asn Ala Ile Asn Ser Gln Thr Asn Arg Ser Gly Phe Val
            20                  25                  30

Lys Gly Val Met Glu Ser Thr Phe Tyr Ser Ala Gly Gln Arg Tyr Asn
            35                  40                  45

Val Met Val Phe Asn Leu Asn Gln Asn Tyr Glu Asp Arg Phe Asn Gly
 50                  55                  60

Val Lys Phe Phe Gly Thr Thr Val Leu Asp Gly Ile Thr Phe Gly Ile
 65                  70                  75                  80

Trp Val Phe Glu Asp Gly Glu Phe Thr Asn Lys Gly Asp Gly Gly Trp
                85                  90                  95

Ile Asn Trp Ala Phe Arg Gly Trp Phe Asp Arg Asp Gly Gly His Val
            100                 105                 110

Lys Phe Tyr Arg Pro
        115

<210> SEQ ID NO 68
<211> LENGTH: 4
<212> TYPE: PRT
<213> ORGANISM: Artificial
<220> FEATURE:
<223> OTHER INFORMATION: bp005 mutant

<400> SEQUENCE: 68

Lys Asp Glu Leu
 1

<210> SEQ ID NO 69
<211> LENGTH: 543
<212> TYPE: DNA
<213> ORGANISM: Bacillus cereus

<400> SEQUENCE: 69
atgaaaaaaa tgaaaaagtt agtgaacatt gctttagccg gaactatcgg tttaggaggt      60
ttgggagcgt ttgcgccaac agatgcaagt gcagctgagg tctctcctgc taaaactaat     120
attcctacta atctatctac tgaattacct actaattttg tagagtctaa gttaccaaat     180

```
gcagcaaaag ctagtgcgaa tttagatgta agtatagatg tattaggtat cgctaatttg    240
attaggaatg ctattaatag tcaaactaat cgttcaggat ttgtaaaagg tgtaatggaa    300
tcaacatttt attctgcagg tcaacgttat aatgttatgg tttttaactt aaaccaaaac    360
tatgaggatc gttttaacgg tgttaaattc tttggaacaa cagtatatga tggaatcact    420
tttggaattt gggtatttga ggatggggaa ttcacgaata aaggtgatgg tggatggatt    480
aactgggcat ttagaggttg gttcgatcgt gatggtggcc atgttaaatt ttatcgccca    540
taa                                                                  543
```

<210> SEQ ID NO 70
<211> LENGTH: 351
<212> TYPE: DNA
<213> ORGANISM: Bacillus cereus

<400> SEQUENCE: 70

```
atgagtgcga atttagatgt aagtatagat gtattaggta tcgctaattt gattaggaat     60
gctattaata gtcaaactaa tcgttcagga tttgtaaaag gtgtaatgga atcaacattt    120
tattctgcag gtcaacgtta taatgttatg gtttttaact taaaccaaaa ctatgaggat    180
cgttttaacg gtgttaaatt ctttggaaca acagtatatg atggaatcac ttttggaatt    240
tgggtatttg aggatgggga attcacgaat aaaggtgatg gtggatggat taactgggca    300
tttagaggtt ggttcgatcg tgatggtggc catgttaaat tttatcgccc a             351
```

<210> SEQ ID NO 71
<211> LENGTH: 294
<212> TYPE: DNA
<213> ORGANISM: Bacillus cereus

<400> SEQUENCE: 71

```
atggctatta atagtcaaac taatcgttca ggatttgtaa aaggtgtaat ggaatcaaca     60
ttttattctg caggtcaacg ttataatgtt atggttttta acttaaacca aaactatgag    120
gatcgtttta acggtgttaa attctttgga acaacagtat atgatggaat cacttttgga    180
atttgggtat ttgaggatgg ggaattcacg aataaaggtg atggtggatg gattaactgg    240
gcatttagag gttggttcga tcgtgatggt ggccatgtta aattttatcg ccca          294
```

<210> SEQ ID NO 72
<211> LENGTH: 537
<212> TYPE: DNA
<213> ORGANISM: Bacillus cereus

<400> SEQUENCE: 72

```
atggggaaaa tgaaaaaagc cactggatta ttattaactg gcatgctagc tattagtgga     60
atttgtacgg ttgggacatc tcaagcaagt gcagaagtaa cacctgcacc cacgactaac    120
aaaaatataa gtttacctta ctctccactc gatccaatat taaacaaaga aaatgctaac    180
aaagtagatg gtcaattaaa tgtcaacatc gatgttctag gtattgccaa tatgattcga    240
gatgctatta atgcgcaaac caatcgctct ggttttgtaa aaggtgtaat ggagtccact    300
ttctatgcag caggacaacg ttacaacgta atggtgttta acttaaacca aaactattct    360
gatcagttta atggtgttaa gttcttcggt actactgttt atgatggtat cacttttggt    420
atttgggtgt ttgaagatgg tgagttcact aatcaaggtg atggtggatg gattaactgg    480
gcatttagag gttggttcga acggaatggt ggtcacgtca aattccatcg accataa       537
```
<210> SEQ ID NO 73
<211> LENGTH: 354
<212> TYPE: DNA
<213> ORGANISM: Bacillus cereus

<400> SEQUENCE: 73

```
atggatggtc aattaaatgt caacatcgat gttctaggta ttgccaatat gattcgagat     60
gctattaatg cgcaaaccaa tcgctctggt tttgtaaaag gtgtaatgga gtccactttc    120
tatgcagcag gacaacgtta caacgtaatg gtgtttaact taaaccaaaa ctattctgat    180
cagtttaatg gtgttaagtt cttcggtact actgtttatg atggtatcac ttttggtatt    240
tgggtgtttg aagatggtga gttcactaat caaggtgatg gtggatggat taactgggca    300
tttagaggtt ggttcgaacg gaatggtggt cacgtcaaat tccatcgacc ataa          354
```

<210> SEQ ID NO 74
<211> LENGTH: 462
<212> TYPE: DNA
<213> ORGANISM: Bacillus cereus

<400> SEQUENCE: 74

```
ttggcttttg caccaaaaga tgctagtgca gctgagattc ctaaagctac tatctctaca     60
gaacctcaat taacaaacaa ggtagaaaat gagaaagcgg tcaagagttt tggtgcaaat    120
ctgaatgtaa atttagatgt tttaggaatt actgatcgga ttataggtgc tattaatagt    180
agcgctaacc gagcaggatt tgtaaaggga gttaaagaaa cagcttttta ttcagcaggc    240
caacagtaca atgttatggt ttttaactta aaccaaaact atgaggatcg ttttaacggt    300
gttaaattct ttggaacaac agtatatgat ggaatcactt ttggaatttg ggtatttgag    360
gatggggaat tcacgaataa aggtgatggt ggatggatta actgggcatt tagaggctgg    420
ttcgatcgtg atggtggcca tgttaaattt tatcgcccat aa                       462
```

<210> SEQ ID NO 75
<211> LENGTH: 354
<212> TYPE: DNA
<213> ORGANISM: Bacillus cereus

<400> SEQUENCE: 75

```
atgggtgcaa atctgaatgt aaatttagat gttttaggaa ttactgatcg gattataggt     60
gctattaata gtagcgctaa ccgagcagga tttgtaaagg gagttaaaga aacagctttt    120
tattcagcag gccaacagta caatgttatg gtttttaact taaaccaaaa ctatgaggat    180
cgttttaacg gtgttaaatt ctttggaaca acagtatatg atggaatcac ttttggaatt    240
tgggtatttg aggatgggga attcacgaat aaaggtgatg gtggatggat taactgggca    300
tttagaggct ggttcgatcg tgatggtggc catgttaaat tttatcgccc ataa          354
```

<210> SEQ ID NO 76
<211> LENGTH: 531
<212> TYPE: DNA
<213> ORGANISM: Bacillus cytotoxicus

<400> SEQUENCE: 76

```
atgaaaaagt tggcgaatat tgctttagct ggagctatcg gtttaggagg attaggagta     60
tttgcaccaa cagatgcaag tgcggctgag atctctcctt ctacaacaaa tgttcctact    120
aacctatcta ctgaattacc tagtaatttt gtagagtcta agttactaaa agaagcgaaa    180
gctagtgcaa atttagatgt aagtatagat gtattaggta tcgctaatat gattagggat    240
```

```
gccatcaata ctcaaactaa tcgttcagga tttgtaaaag gcgtaatgga atcaacattt    300
tatgctgcag gtcaacgtta taatgttatg gttttttaatt taaaccaaaa ctatgatgat    360
cgttttaacg gtgttaaatt cttcggaaca acagtatatg atggaatcac ttttggaatt    420
tgggtatttg aagatggaga atttacgaat caaggtgatg gtggatggat taactgggca    480
tttagaggtt ggttcgatcg taatggtaac catgttaaat ttcatcgtgc a             531
```

```
<210> SEQ ID NO 77
<211> LENGTH: 540
<212> TYPE: DNA
<213> ORGANISM: Bacillus cereus

<400> SEQUENCE: 77
atgaaaaatt tgaaaaagtt agtgaacatt gctttagccg gaactatcgg tttaggaggt    60
ttgggagcgt ttgcgccaac agatgcaagt gcagctgagg tctctcctgc taaaactaat    120
attcctacta atctatctac tgaattacct actaattttg tagagtctaa gttaccaaat    180
gcagcaaaag ctagtgcgaa tttagatgta agtatagatg tattaggtat cgctaatttg    240
ataaggaaag ctattaatag tcaaactaat cgttcaggat tgtaaaagg tgtaatggaa     300 tcaacatttt attctgcagg tcaacgatat aatgtaaagg atattaactt aaaccaaaac    360
tatgaggatc gttttaacgg tgttaaatta tttggaacaa cagtatatga tggtatcact    420
tttggaattt gtatatttga tgaagggaa ttcacgaata aggtgatgg tggatggatt    480 aactgggcat ttagaggttg gttcgatcgt gatggtggcc atgttaaatt ttatcgccca    540
```

```
<210> SEQ ID NO 78
<211> LENGTH: 540
<212> TYPE: DNA
<213> ORGANISM: Bacillus cytotoxicus

<400> SEQUENCE: 78
atgaaaaaaa taaaaaagtt ggcgaacatt gctttagctg gagctatcgg tttaggagga    60
ttaggagtgt ttgcaccaat tgatgcaagt gcggctgaga tctctcctcc tacaacaaat    120
gttcctacta acctatctac tgaattacct agtaattttg tagagtctaa gttaccaaaa    180
gaagcaaaag ctagtgcaaa tttaaatgta agtatagatg tattaggtat cgctaatatg    240
attagggatg ccatcaatac tcaaactaac cgttcaggat ttgtaaaagg tgtaatggaa    300
tcaacatttt attctgcagg tcaacgttat aatgttatgg tttttaattt aaaccaaaac    360
tatgatgatc gttttaacgg tgttaaattc ttcggaacaa cagtatataa tggaatcact    420
tttggaattt gggtatttga agatggggaa tttacgaatc aaggtgatgg tggatggatt    480
aactgggcat ttagaggttg gttcgatcgt aatggtaacc atgttaaatt tcatcgtcca    540
```

```
<210> SEQ ID NO 79
<211> LENGTH: 540
<212> TYPE: DNA
<213> ORGANISM: Bacillus pumilus

<400> SEQUENCE: 79
atgaaaaaaa tgaaaaagtt agtgaacatt gctttagccg gaactatcgg tttaggaggt    60
ttgggagcgt ttgcgccaac agatgcaagt gcagctgagg tctctcctgc taaaactaat    120
attcctacta atctatctac tgaattacct actaattttg tagagtctaa gttaccaaat    180
gcagcaaaag ctagtgcaaa tttagatgta agtatagatg tattaggtat cgctaatttg    240
attaggaatg ctattaatag tcaaactaat cgttcaggat tgtaaaagg tgtaattgaa    300
```

```
tcaacatttt attcagcttg tcaactttat aatgttattg tttttaactt aaaccataac    360
tatgaggata ggtttaactt tgttaaattc tttggaacaa cagtatatga tggaatcact    420
tttggaattt gggtatttga ggatggggaa ttcacgaata aaggtgatgg tggatggatt    480
aactgggcat ttagaggttg gttcgatcgt gatggtggcc atgttaaatt ttatcgccca    540
```

<210> SEQ ID NO 80
<211> LENGTH: 483
<212> TYPE: DNA
<213> ORGANISM: Bacillus thuringiensis

<400> SEQUENCE: 80

```
atgttaggag tgtttactcc aacagatgca agtgcggatg agatttctcc tgctacaaca     60
aatatcccta ctaacctatc tactgaatta cctattaatt ttgtagagtc taagtttaca    120
aaagcagcga aagctagtgc aaatttagat gtaagtatag atgtattagg tatcgctaat    180
atgattagag acgccatcaa tgctcaaacg aatcgttcag ggtttgtaaa aggcgtaatg    240
gaatcaacat tttatgcggc aggtcaacgc tataatgtta tggttttttaa tttaaaccaa    300 aactataatg atcgttttaa cggtgttaag ttcttcggta caacagtata tgatggaatc    360
acttttggaa tttgggtatt tgaagacggg gaatttacga atcaaggtga tggtggatgg    420
attaactggg catttagagg ttggttcgat cgtaatggta accatgttaa attttatcgt    480
cca                                                                 483
```

<210> SEQ ID NO 81
<211> LENGTH: 540
<212> TYPE: DNA
<213> ORGANISM: Bacillus cytotoxicus

<400> SEQUENCE: 81

```
atgaaaaaaa tgaaaaagtt gacgaacatt gctttagctg gagctatcgg tttaggcgga     60
ttaggagtgt ttgcaccaac agatgcaagt gcggctgaga catctccttc tacaacaaat    120
gttcctacta acctatctac tgaattacct attaattttg tagagtctaa tttaccaaca    180
gcagcgaaag ctagtgcaaa tttagatgta agtatagatg tattaggtat cgctaacatg    240
attaggaatt ccatcaatac tcagactaac cgttcaggat ttgtaaaagg cgtaatggaa    300
tcaacatttt attctgcagg tcaacgctat aatgttatgg ttttttaattt aaaccaaaac    360 tataatgatc gttttaacgg tgttaaattc ttcggaacaa cagtatatga tggaatcact    420
tttggaattt gggtatttga agatggggaa tttacgaatc aaggtgatgg tggatggatt    480
aactgggcat ttagaggttg gttcgatcgt aatggtaacc atgttaaatt tcatcgtcaa    540
```

<210> SEQ ID NO 82
<211> LENGTH: 540
<212> TYPE: DNA
<213> ORGANISM: Bacillus thuringiensis

<400> SEQUENCE: 82

```
atgaaaaaaa tgaaaaagtt agtgaacatt gcgttagccg gaactatcgg tttaggaggg     60
ttgggagcat ttgcaccaac agatgcaagt gcagctgagg tctctcctgc taaaactaat    120
attcctacta acctatctac tgaatttcct actaattttg tagagtctaa gttaccaaat    180
gcagcgaaag ctagtgcgaa tttagatgta agtatagatg tattaggtat cgctaatttg    240
attaggaatc tattaataga tcaaactaat cgttcaggat ttgtaaaagg tgtaatggaa    300
tcaacatttt attctgcagg tcaacgttat aatgttatgg ttttttaactt aaaccaaaac    360
```

```
tatgaggatc gttttaacgg tgttaaattc ttaggaacaa cagtatatga tggaatcact    420
tttggaattt gggtatttga ggatggggaa ttcacgaata aggtgatgg tggatggata    480 aagatggcat ttagaggtag gatcgatcgt gatgctcaca ctgttaaatt ttatcgccaa    540
```

```
<210> SEQ ID NO 83
<211> LENGTH: 540
<212> TYPE: DNA
<213> ORGANISM: Bacillus thuringiensis

<400> SEQUENCE: 83
atgaaaaaaa ttcaaaaatt taggaacatt gctttagctg gagctatcgg tttaggaggc    60
ttaggagcgt ttgcaccaac taatgcaagt gcagccgaga cctctccgtc aacaacaaat   120
gtttctgcta atctacctac tgaattacct attaattttg tagagtctca attaccaaaa   180
aaagcggaag ctagtgcaaa tttaaatgta aatgtggacg tattgggtat cgctaatatg   240
attagagatg ctatcaatgc ccaaactaat cgttcaggat tgtaaaagg cgtaatggaa   300 tcaacatttt acgctgcggg tcaacgctat aatgttatgg ttttaatttt aaaccaaaac   360
tatcaggatc gctttaacgg tgttaaattc ttcggtacaa cggtatatga tggaatcact   420
tttggtattt gggtatttga agatggtgaa ttcacgaatc aaggcgatgg cggatggatt   480
aactgggcat ttagaggttg gtttgatcgt aatggtggcc atgttaaatt ttatcgtgga   540
```

```
<210> SEQ ID NO 84
<211> LENGTH: 540
<212> TYPE: DNA
<213> ORGANISM: Bacillus weihenstephanensis

<400> SEQUENCE: 84
atgaaaaaaa tgaaaaagtt ggcgaacatt gctttagctg gagctatcgg tttaggagga    60 tgggagcgt tcgcaccaac agatgcaagt gcggctgaga tctctccttc tacaacaaat   120
gttcctacta acctatctac tgaattacct agtaattttg tagagtctca gttaccaaaa   180
gaagcgaaag ctagtgcaaa tttaagtgta aatgtagacg tattgggtat cgctaatatg   240
gttagagatg ctattaatgc tcaaactaat cgttcaggat tgtaaaagg cgtaatggaa   300 tcaacatttt atgctgcagg tcaacgctat aatgttatgg ttttaatttt aaaccaaaac   360
tatgatgatc gttttaacgg tgttaaattc ttcggaacaa cagtatatga tggaatcact   420
tttggaattt gggtatttga agatggggaa tttacgaatc aaggtgatgg tggatggatt   480
aactgggcat ttagaggttg gttcgatcgt aatggtaacc atgtgaaatt tcatcgtgca   540
```

```
<210> SEQ ID NO 85
<211> LENGTH: 531
<212> TYPE: DNA
<213> ORGANISM: Bacillus thuringiensis

<400> SEQUENCE: 85
atgaaaaagt tggcgaatat tgctttagct ggagctatcg gtttaggagg attaggagta    60
tttgcaccaa cagatgcaag tgcggctgag atctctcctt ctacaacaaa tgttcctact   120
aacctatcta ctgaattacc aagtaatttt gtagaatcta gttaccaaa agaagcgaaa   180 gctagtgcga atttagatgt aagtatagat gtattaggta tcgctaatat gattagggat   240
gccatcaatg ctcaaactaa tcgttcagga tttgtaaaag cgtaatgga atcaacattt   300 tatgctgcag gtcaacgtta taatgttatg gttttaatt taaaccaaaa ctatgatgat   360
cgttttaacg gtgttaaatt cttcggaaca acagtatatg atggaatcac ttttggaatt   420
```

```
tgggtatttg aagatggaga atttacgaat caaggtgatg gtggatggat taactgggca    480
tttagaggtt ggttcgatcg taatggtaac catgttaaat tcatcgtgc a              531
```

<210> SEQ ID NO 86
<211> LENGTH: 540
<212> TYPE: DNA
<213> ORGANISM: Bacillus cytotoxicus

<400> SEQUENCE: 86

```
atgaaaaaaa tgaaaaagtt gacgaacatt gctttagctg gagctatcgg tttaggagga    60
ttaggagtgt ttgcaccaac agatgcaagt gcagctgaga tctctccttc tacaacaaat    120
gttcctacta acctatctac tgaattacct agtaattttg tagagtctaa gttaccaaaa    180
gaagcacaag ctagtgcaaa tttaaatgta agtatagatg tattaggtat cgctaatatg    240
attagggatg ccatcaatac tcaaactaat cgttcaggat ttgtaaaagg cgtaatggaa    300
tcaacatttt attctgcagg tcaacgctat aatgttatgg ttttaatttt aaaccaaaac    360
tatgatgatc gttttaacgg tgttaaattc ttcggaacaa cagtatatga tggaatcact    420
tttggaattt gggtatttga agatggggaa tttacgaatc aaggtgatgg tggatggatt    480
aactgggcat ttagaggttg gttcgatcgt aatggtaacc atgttaaatt tcatcgtcca    540
```

<210> SEQ ID NO 87
<211> LENGTH: 540
<212> TYPE: DNA
<213> ORGANISM: Bacillus cytotoxicus

<400> SEQUENCE: 87

```
atgaaaaaaa tgaaaaagtt gacgaacatt gctttagctg gagctatcgg tttaggcgga    60
ttaggagtgt ttgcaccaac agatgcaagt gcggctgaga cttctccttc tacaacaaat    120
gttcctacta acctatctac tgaattacct attaattttg tagagtctaa tttaccaaca    180
gcagcgaaag ctagtgcaaa tttagatgta agtatagatg tattaggtat cgctaacatg    240
attaggaatt ccatcaatac tcagactaac cgttcaggat ttgtaaaagg cgtaatggaa    300
tcaacatttt attctgcagg tcaacgctat aatgttatgg ttttaatttt aaaccaaaac    360
tataatgatc gttttaacgg tgttaaattc ttcggaacaa cagtatatga tggaatcact    420
tttggaattt gggtatttga agatggggaa tttacgaatc aaggtgatgg tggatggatt    480
aactgggcat ttagaggttg gttcgatcgt aatggtaacc atgttaaatt tcatcgtcca    540
```

<210> SEQ ID NO 88
<211> LENGTH: 540
<212> TYPE: DNA
<213> ORGANISM: Bacillus thuringiensis

<400> SEQUENCE: 88

```
atgaaaaaaa tgaaaaagtt ggcgaatgtt gctttagctg gagctatcgg tttagggga     60 ttgggggcgt ttgcaccaac agatgcaagt gcagctgaaa tctctccttc taaaacaaat    120
attcctacta acctatctac tgaattacct actaattttg tagagtctaa gttaccaaac    180
gcagcgaaag ctagtgcaaa tttagatgta agtatagatg tattaggtat tgctaatatg    240
attagggatg ccatcaatgc tcaaactaat cgttcaggat ttgtaaaagg cgtaatggaa    300
tcaacatttt atgctgcagg tcaacgttat aatgttatgg ttttaatttt aaaccaaaac    360
tatgatgatc gttttaacgg tgttaaattc ttcggaacaa cagtatatga tggaatcact    420
```

```
tttggaattt gggtatttga agatggggaa tttacgaatc aaggtgatgg tggatggatt    480
aactgggcat ttagaggttg gttcgatcgt gatggtggcc atgttaaatt ttatcgccca    540
```

<210> SEQ ID NO 89
<211> LENGTH: 327
<212> TYPE: DNA
<213> ORGANISM: Bacillus weihenstephanensis

<400> SEQUENCE: 89

```
atggacgtgt tgggtattgc taatatgatt agggatgcta tcaatacccca aactaatcgc     60 tcaggatttg taaaaggcgt aatggaatca acattttacg ctgcaggtca acgctataat    120
gttatggttt ttaatttaaa ccaaaactat caggatcgct taacggtgt taaattcttc     180 ggtacaacgg tatatgatgg aatcactttt ggaatttggg tatttgaaga tggtgaattt    240
acgaatcaag gtgatggtgg atggattaac tgggcattta gaggttggtt tgaccgtaat    300
ggtggccatg ttaaatttta tcgtgga                                        327
```

<210> SEQ ID NO 90
<211> LENGTH: 531
<212> TYPE: DNA
<213> ORGANISM: Bacillus weihenstephanensis

<400> SEQUENCE: 90

```
atgaaaaaaa tgaagaagtt agggaacatt gctttagctg gagctatcgg tttaggagcg     60
tttgtaccaa ctaatgcaag tgcggccgag atttctccgt ctacaacaac tgttcctgct    120
aatctatcta ctgaattacc tattaatttt gtagagtctc aattaccaaa agaggcgaaa    180
gctagtgcaa atttaagtgt aaatgtggac gtgttgggta ttgctaatat gattagggat    240
gctatcaata cccaaactaa tcgctcagga tttgtaaaag gcgtaatgga atcaacattt    300
tacgctgcag gtcaacgcta taatgttatg gttttttaatt taaaccaaaa ctatcaggat    360
cgctttaacg gtgttaaatt cttcggtaca acggtatatg atggaatcac ttttggaatt    420
tgggtatttg aagatggtga atttacgaat caaggtgatg gtggatggat taactgggca    480
tttagaggtt ggtttgaccg taatggtggc catgttaaat tttatcgtgg a             531
```

<210> SEQ ID NO 91
<211> LENGTH: 534
<212> TYPE: DNA
<213> ORGANISM: Bacillus cereus

<400> SEQUENCE: 91

```
atggggaaaa tgaaaaaagc cactggatta ttattaactg gcatgctagc tattagtgga     60
atttgtacgg ttgggacatc tcaagcaagt gcagaagtaa cacctgcacc cacgactaac    120
aaaaatataa gtttaccttta ctctccactc gatccaatat aaacaaaga aaatgctaac    180 aaagtagatg gtcaattaaa tgtcaacatc gatgttctag gtattgccaa tatgattcga    240
gatgctatta atgcgcaaac caatcgctct ggttttgtaa aaggtgtaat ggagtccact    300
ttctatgcag caggacaacg ttacaacgta atggtgttta acttaaacca aaactattct    360
gatcagttta atggtgttaa gttcttcggt actactgttt atgatggtat cacttttggt    420
atttgggtgt tgaagatgg tgagttcact aatcaaggtg atggtggatg gattaactgg    480
gcatttagag gttggttcga acggaatggt ggtcacgtca aattccatcg acca         534
```

<210> SEQ ID NO 92
<211> LENGTH: 540
<212> TYPE: DNA
<213> ORGANISM: Bacillus thuringiensis

<400> SEQUENCE: 92

```
atgaaaaaaa tgaagaagtt agggaacatt gctttagctg gagctatcgg tctaggaggt      60
ttaggagcgt ttgtaccaac taatgcaagt gcggccgaga tttctccgtc tacaacaact     120
gttcctgcta atctatctac tgaattacct attaattttg tagagtctca attaccaaaa     180
gaggcgaaag ctagtgcaaa tttaagtgta aatgtggacg tgctgggtat tgctaatatg     240
attagggatg ctatcaatgc ccaaactaat cgctcaggat ttgtaaaagg cgtaatggaa     300
tcaacatttt acgctgcagg tcaacgctat aatgttatgg ttttaatt aaaccaaaac      360
tatcaggatc gctttaacgg tgttaaattc ttcggtacaa cggtatatga tggaatcact     420
tttggaattt gggtatttga agatggtgaa tttacgaatc aaggtgatgg cggatggatt     480
aactgggcat ttagaggttg gtttgaccgt aatggtggcc atgttaaatt ttatcgtgga     540
```

<210> SEQ ID NO 93
<211> LENGTH: 543
<212> TYPE: DNA
<213> ORGANISM: Bacillus thuringiensis

<400> SEQUENCE: 93

```
atgaaaaaaa tgaaaaagtt agtgaacatt gctttagccg gaactatcgg tttaggaggt      60
ttgggagcgt ttgcgccaac agatgcaagt gcagctgagg tctctcctgc taaaactaat     120
attcctacta atctatctac tgaattacct actaattttg tagagtctaa gttaccaaat     180
gcagcaaaag ctagtgcaaa tttagatgta agtatagatg tattaggtat cgctaatttg     240
attaggaatg ctattaatag ccaaactaat cgttcaggat ttgtaaaagg tgtaatggaa     300
tcaacatttt tttcagcagg tcaacgttat tatgttatgg ttttaactt aaaccaaaac      360
tatgaggatc gttttaacgg tgttaaattc tttggaacaa cagtatatga tggaatcact     420
tttggaattt gggtatttga agattgtgaa ttcaagaata aggtgatgg tggttggtat      480
aactggtcat taagaggatg gttcgataga gatggtggcc atgttatatt ttatcgacct     540
tta                                                                    543
```

<210> SEQ ID NO 94
<211> LENGTH: 387
<212> TYPE: DNA
<213> ORGANISM: Bacillus thuringiensis

<400> SEQUENCE: 94

```
atgtttgtag agtctaagtt accaaatgca acaaaagcta gtgcaaattt agatgtaagt      60
atagatgtat taggtatcgc taatttgatt aggaatgcta ttaatagtca aactaatcgt     120
tcaggatatg taataggtga aatggattca acaattaata cagcaggtca acgttataat     180
gttatggtat ttatcttaaa ccaaaactat gaggatcgtt taacggtgt taatttcttt      240
ggaacaacag tttatgatgg attcactttt ggaattagtg catttgaaga tggggaattc     300
acgaataaag gtgatggtgg atggattaac tgggcattta gaggttggtt cgatcgtgat     360
ggtggccatg ttaaatttta tcgccca                                         387
```

<210> SEQ ID NO 95
<211> LENGTH: 540
<212> TYPE: DNA
<213> ORGANISM: Bacillus thuringiensis

<400> SEQUENCE: 95

```
atgaaaaaaa tgaaaaagtt agtgaacatt gctttagccg gaactatcgg tgtaggaggt    60
ttgggagcgt ttgcgccaac agatgcaagt gcagctgagg tctctcctgc taaaactaat   120
attcctacta atctatctac tgaattacct actaattttg tagagtctaa gttaccaaat   180
gcagcaaaag ctagagcgaa tttagatgta agtatagatg tattaggtat cgctaatttg   240
attaggaatg ctattaatag tcatactaat cgttcaggat ttgtaaatgg tgtaatggaa   300
tcaacatttt attctgcagg tcaacgttat aatgttattg ttttaaactt aaaccatatc   360
tatgaggatc gttttaactg tgttaaattc tttggaacaa cagtatatga tggaatcact   420
tttggaattt gggtatttga ggatggggaa ttctcgaata aggtgatgg tggatggatt   480 aactgggcat ttagaggttg gttcgatcgt gatggtggcc atgttaaatt ttatcgccca   540
```

<210> SEQ ID NO 96
<211> LENGTH: 360
<212> TYPE: DNA
<213> ORGANISM: Bacillus thuringiensis

<400> SEQUENCE: 96

```
atgataaaag ctagtgaaaa tttagatgga agtatagatg tattatgttt cgctaatttg    60
attaggaatg tttttaatag tcatactaat cgttcaggat ttgtaaaagg tgtaatggaa   120
tcaacatttt attcagcagg gcaacgttat aatgttatgg tttttaactt aaaccaaaac   180
tatgaggatc gttttaacgg tgttaaattc attggaacaa cagtatatga tggaatcact   240
tttggaattt gggtatttga agatggggaa ttcacgaata aggtgatgg tggatggatt   300 aactgggcat ttagaggttg gttcgatcgt gatggtggcc atgttaaatt ttatcgccca   360
```

<210> SEQ ID NO 97
<211> LENGTH: 459
<212> TYPE: DNA
<213> ORGANISM: Bacillus cereus

<400> SEQUENCE: 97

```
atggcttttg caccaaaaga tgctagtgca gctgagattc ctaaagctac tatctctaca    60
gaacctcaat taacaaacaa ggtagaaaat gagaaagcgg tcaagagttt tggtgcaaat   120
ctgaatgtaa atttagatgt tttaggaatt actgatcgga ttataggtgc tattaatagt   180
agcgctaacc gagcaggatt tgtaaaggga gttaagaaaa cagctttta ttcagcaggc   240 caacagtaca atgttatggt ttttaactta aaccaaaact atgaggatcg ttttaacggt   300
gttaaattct ttggaacaac agtatatgat ggaatcactt ttggaatttg ggtatttgag   360
gatggggaat tcacgaataa aggtgatggt ggatggatta actgggcatt tagaggctgg   420
ttcgatcgtg atggtggcca tgttaaattt tatcgccca                           459
```

<210> SEQ ID NO 98
<211> LENGTH: 540
<212> TYPE: DNA
<213> ORGANISM: Bacillus thuringiensis

<400> SEQUENCE: 98

```
atgaaaaaaa tgaaaaagtt agtgaacatt gcgttagccg gaactatcgg tttaggaggg    60
ttgggagcat ttgcaccaac agatgcaagt gcagctgagg tctctcctgc taaaactaat   120
attcctacta acctatctac tgaattacct actaattttg tagagtctaa gttaccaaat   180
gcagcgaaag ctagtgcgaa tttagatgta agtatagatg tattaggtat cgctaatttg   240
attaggaatg ctattaatag tcaaactaat cgttcaggat tgtaaaagg tgtaatggaa    300
tcaacatttt attctgcagg tcaacgttat aatgttatgg ttttaacttt aaaccaaaac   360
tatgaggatc gttttaacgg tattaaattc tttggaacaa cagtatatga tggaatcact   420
tttggaattt gggtatttga ggatgtggta ttcacgaata aaggtgatgg tggatggatt   480
aactggtcat ttagatgttt gttcgatctt gatggtggcc atgttaaatt ttatcgccca   540
```

<210> SEQ ID NO 99
<211> LENGTH: 513
<212> TYPE: DNA
<213> ORGANISM: Bacillus thuringiensis

<400> SEQUENCE: 99

```
atggctttag ctgtagctat cggtttagga ggattaggag tctttgcacc aacagatgca    60
agtgcggctg agatctctcc ttctacaaca aatgttccta ctaatctatc tactgaatta   120
cctagtaatt tgtagagtc taagttgcca aaagaagcga agctagtgc aaatttaaat    180
gtaagtatag atgtattagg tatcgctaat atgattaagg atgccatcaa tgctcaaact   240
aatcgttcag gatttgtaaa aggcgtaatg gaatcaacat tttatgctgc tggtcaacgc   300
tataatgtta tggtttttaa tttaaaccaa aactatgatg atcgctttaa cggtgttaaa   360
ttcttcggaa caacagtata tgatggaatc acttttggaa tttgggtatt tgaagatggg   420
gaatttacaa atcaaggtga tggtggatgg attaactggg catttagagg ttggttcgat   480
cgtaatggta accatgttaa atttcatcgt gca                                513
```

<210> SEQ ID NO 100
<211> LENGTH: 540
<212> TYPE: DNA
<213> ORGANISM: Bacillus thuringiensis

<400> SEQUENCE: 100

```
atgaaaaaaa caaaaaagtt ggcgaacatt gctttagctg tagctatcgg tttaggagga    60
ttaggagtct ttgcaccaac agatgcaagt gcggctgaga tctctccttc tacaacaaat   120
gttcctacta atctatctac tgaattacct agtaattttg tagagtctaa gttgccaaaa   180
gaagcgaaag ctagtgcaaa tttaaatgta agtatagatg tattaggtat cgctaatatg   240
attaaggatg ccatcaatgc tcaaactaat cgttcaggat tgtaaaagg cgtaatggaa    300
tcaacatttt atgctgctgg tcaacgctat aatgttatgg ttttaatttt aaaccaatac   360
tatgatgatc gctttaacgg tgttaaattc ttcggaacaa cagtatatga tggaatcact   420
tttggaattt gggtatttga agatggggaa tttacaaatc aaggtgatgg tggatggatt   480
aactgggcat ttagaggttg gttcgatcgt aatggtaacc atgttaaatt tcatcgtgca   540
```

<210> SEQ ID NO 101
<211> LENGTH: 540
<212> TYPE: DNA
<213> ORGANISM: Bacillus cytotoxicus

<400> SEQUENCE: 101

```
atgaaaaaaa tgaaaaagtt gacgaacatt gctttagctg gagctatcgg tttaggagga    60
ctaggagtgt tgcaccaac agatgcaagt gcggctgagg tctctccttc tacaacaaat   120
gttcctacta acctatctac tgaattacct attaattttg tagagtctaa tttaccaaaa   180
gcagcgaaag ctagtgcaaa tttaaatgta agtatagatg tattaggtat tgctaatatg   240
attaagaatt ccatcaatac tcaaactaac cgttcaggat ttgtaaaagg cgtaatggaa   300
tcaacatttt attctgcagg tcaacgctat aatgttatgg tttttaattt aaaccaaaac   360
tataatgatc gttttaacgg tgttaaattc ttcggaacaa cagtatatga tggaatcact   420
tttggaattt gggtatttga agatggggaa ttcacgaatc aaggtgatgg tggatggatt   480
aactgggcat ttagaggttg gttcgatcgc aatggtaacc atgttaaatt tcatcgtcca   540
```

<210> SEQ ID NO 102
<211> LENGTH: 426
<212> TYPE: DNA
<213> ORGANISM: Bacillus thuringiensis

<400> SEQUENCE: 102

```
atgaatattc ctactaatca atctactgaa ttacctacta atttagtaga gtctaagtta    60
ccaaatgcag caaaagctag tgcaaattta gatgtaagta tagatgtatt aggtatcgct   120
aatttgatta ggaatgctat taatagtcaa actaatcgtt caggaaatgt aaaaggtgta   180
atggaatcaa cattttattc agcaggtcaa cgttataatg ttatggtttt taacttaaac   240
caaaactatg aggatcgttt taacggtggt attttctttg gaacaacagt atttgatgga   300
ttcacttttg gaatttgggt ttttgaagtt ggggaattca cgaataaagg tgatggtgga   360
tggattaact gggcatttag aggttggttc gatcgtgatg gtggccatgt taaattttat   420
cgccca                                                              426
```

<210> SEQ ID NO 103
<211> LENGTH: 540
<212> TYPE: DNA
<213> ORGANISM: Bacillus thuringiensis

<400> SEQUENCE: 103

```
atgaaaaaaa tgaaaaagtt agtgaacatt gctttagccg gaactatcgg tttaggaggt    60
ttgggagcgt ttgcgccaac agatgcaagt gcagctgagg tctctcctgc taaaactaat   120
attcctacta atctatctac tgaattacct actaattttg tagagtctaa gttaccaaat   180
gcagcaaaag ctagtgcgaa tttagatgta agtatagatg tattaggtat cgctaatttg   240
attaggaatg ctattaatag tcaaactaat cgttcaggat ttgtaaaagg tgtaatggaa   300
tctacatttt attctgcagg tcaacgttat aatgttatgg tttttaactt aaaccaaaac   360
tatgaggatc gttttaacgg tattaaattc tttggaacaa cagtatatga tggaatcact   420
tttggaattt gggtatttga ggatggggaa ttcacgaata aggtgaagg tggatggatt   480
aactgggaat ttagagtttg gttagatcga gatggtggcc ttgttaaatt ttatcgccca   540
```

<210> SEQ ID NO 104
<211> LENGTH: 540
<212> TYPE: DNA
<213> ORGANISM: Bacillus thuringiensis

```
<400> SEQUENCE: 104
atgaaaaaaa tgaaaaagtt aggaaacatt gctttagctg gagctatcgg tttaggaggt    60
ttaggagcgt ttgcaccaac taatgcaagt gcggctgaga tctctccgtc tacaacaaat   120
gttcctgcta atctatctac taaattacct attaattttg tagagtctca attaccaaaa   180
gaatcgaaag ctagtgcaaa tttaagtgta aatgtcgacg tattgggtat cgctaatatg   240
attagggatg ctattaatac tcaaactaat cgttcaggat ttgtaaaagg cgtaatggaa   300
tcaacatttt acgctgcagg tcaacgctat aatgttatgg ttttaatttt aaaccaaaac   360
tatcaggatc gctttaacgg tgttaaattc ttcggtacaa cggtatatga tggaatcact   420
tttggaattt gggtatttga agatggtgaa tttacgaatc aaggtgatgg tggatggatt   480
aactgggcat tagaggttg gtttgatcgc gatggtggtt atgttaaatt ttatcgtgga    540

<210> SEQ ID NO 105
<211> LENGTH: 462
<212> TYPE: DNA
<213> ORGANISM: Bacillus pumilus

<400> SEQUENCE: 105
atggatgcaa gtgcggctga gatctctcct tctacaacaa atgttcctac taatctatct    60
actgaattac ctagtaattt tgtagagtct aagttgccaa agaagcgaa agctagtgca   120 aatttaaatg taagtataga tgtattaggt atcgctaata tgattaagga tgccatcaat   180
gctcaaacta atcgttcagg atttgtaaaa ggcgtaatgg aatcaacatt ttatgctgct   240
ggtcaacgct ataatgttat ggttttaatt ttaaaccaaa actatgatga tcgctttaac   300
ggtgttaaat tcttcggaac aacagtatat gatggaatca cttttggaat ttgggtattt   360
gaagatgggg aatttacaaa tcaaggcgat ggtggatgga ttaactgggc atttagaggt   420
tggttcgatc gtaatggtaa ccatgttaaa tttcatcgtg ca                      462

<210> SEQ ID NO 106
<211> LENGTH: 297
<212> TYPE: DNA
<213> ORGANISM: Artificial
<220> FEATURE:
<223> OTHER INFORMATION: bp005 mutant

<400> SEQUENCE: 106
atggcaatta attctcaaac caacagaagt ggctttgtga aggggtgat ggaaagcaca     60 ttttattctg ctggccagag atacaatgtg atggtgttca acctaaacca gaactatgag   120
gacaggttca atggggtgaa gttctttgga accactgttt atgatggcat cacctttggg   180
atttgggtgt tgaggatgg agagttcacc aacaagggag atggaggatg gatcaactgg   240
gccttcagag gctggtttga cagagatgga ggccatgtga agttctacag gccataa      297
```

BP005 TOXIN GENE AND METHODS FOR ITS USE

CROSS REFERENCE TO RELATED APPLICATIONS

This application is a National Stage entry of International Application No. PCT/US2018/014182, filed Jan. 18, 2018, which claims the benefit of U.S. Provisional Application Ser. No. 62/447,592, filed Jan. 18, 2017 the contents of aforementioned applications are herein incorporated by reference in their entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_3000052-039001_ST25.txt" created on 9 Jul. 2019, and 102,152 bytes in size) is submitted concurrently with the instant application, and the entire contents of the Sequence Listing are incorporated herein by reference.

BACKGROUND

Field of the Invention

This invention relates to the field of molecular biology. Provided are novel genes that encode pesticidal proteins. These proteins and the nucleic acid sequences that encode them are useful in preparing pesticidal formulations and in the production of transgenic pest-resistant plants.

Description of Related Art

Insect pests are a major cause of damage to the world's commercially important agricultural crops. Current strategies aimed at reducing crop losses rely primarily on chemical pesticides. The development and cultivation of transgenic crops has revolutionized agriculture worldwide. In 2014, the global cultivation of insect-protected crops was estimated at 78.8 M ha. The first generation of insect-resistant transgenic plants is based on insecticidal proteins from *Bacillus thuringiensis* (Bt). A second generation of insect-resistant plants under development include both Bt and non-Bt proteins with novel modes of action and different spectra of activity against insect pests. Moreover, piercing/sucking insects, which are generally resistant to insecticidal Bt proteins, have emerged as major pests since the introduction of transgenic crops expressing these toxins. Crops expressing Bt insecticidal proteins provide excellent control of economically important coleopteran and lepidopteran pests, but are not effective in controlling hemipteran pests.

Because of the devastation that insects can confer, and the improvement in yield by controlling insect pests, there is a continual need to discover new forms of pesticidal toxins.

SUMMARY

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise bacteria, plants, plant cells, tissues, and seeds comprising the nucleotide sequence of the invention.

In particular, isolated, recombinant and chimeric nucleic acid molecules are provided that encode a pesticidal protein. Additionally, amino acid sequences corresponding to the pesticidal protein are encompassed. In particular, the present invention provides for an isolated, recombinant or chimeric nucleic acid molecule comprising a nucleotide sequence encoding the amino acid sequence shown in any of SEQ ID NO:1-40, 42, 43, 45-48, 50, 51, 52, 54, 56, 58-64, 66, or 67 or a nucleotide sequence set forth in SEQ ID NO:69-106, as well as biologically-active variants and fragments thereof. Nucleotide sequences that are complementary to a nucleotide sequence of the invention, or that hybridize to a sequence of the invention or a complement thereof are also encompassed. Further provided are vectors, host cells, plants, and seeds comprising the nucleotide sequences of the invention, or nucleotide sequences encoding the amino acid sequences of the invention, as well as biologically-active variants and fragments thereof.

Methods are provided for producing the polypeptides of the invention, and for using those polypeptides for controlling or killing a lepidopteran, hemipteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

DETAILED DESCRIPTION OF A PREFERRED EMBODIMENT

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling. The proteins find use in controlling or killing lepidopteran, hemipteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, Hemiptera, and Coleoptera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Thus, provided herein are novel isolated, recombinant or chimeric nucleotide sequences that confer pesticidal activity. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated, recombinant or chimeric nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. Also encompassed herein are nucleotide sequences capable of hybridizing to the nucleotide sequences of the invention under stringent conditions as defined elsewhere herein. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The term "recombinant" encompasses polynucleotides or polypeptides that have been manipulated with respect to the native polynucleotide or polypeptide, such that the polynucleotide or polypeptide differs (e.g., in chemical composition or structure) from what is occurring in nature. In another embodiment, a "recombinant" polynucleotide is free of internal sequences (i.e. introns) that naturally occur in the genomic DNA of the organism from which the polynucleotide is derived. A typical example of such polynucleotide is a so-called Complementary DNA (cDNA).

An isolated, recombinant or chimeric nucleic acid (or DNA) is used herein to refer to a nucleic acid (or DNA) that is no longer in its natural environment, for example in an in vitro or in a recombinant bacterial or plant host cell. In some embodiments, an isolated, recombinant or chimeric nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated bp005 nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a BP005 protein that is substantially free of cellular material includes preparations of protein having less than about 30%, 20%, 10%, or 5% (by dry weight) of non-BP005 protein (also referred to herein as a "contaminating protein"). In some embodiments, the recombinant nucleic acid of the invention comprises one or more nucleotide substitutions relative to any of SEQ ID NO:69-106, or a variant or fragment thereof.

Nucleotide sequences encoding the proteins of the present invention include the sequence set forth in any of SEQ ID NO:69-106, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the pesticidal proteins encoded by these nucleotide sequences are set forth in any of SEQ ID NO:1-40, 42, 43, 45-48, 50, 51, 52, 54, 56, 58-64, 66, or 67.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. Thus, biologically-active fragments of the polypeptides disclosed herein are also encompassed. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. In another embodiment, the pesticidal activity is hemiptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to any of SEQ ID NO:1-40, 42, 43, 45-48, 50, 51, 52, 54, 56, 58-64, 66, or 67. In some embodiments, the fragments encompassed herein result from the removal of the C-terminal crystallization domain, e.g., by proteolysis or by insertion of a stop codon in the coding sequence.

In various embodiments, the nucleic acid of the invention comprises a degenerate nucleic acid of any of SEQ ID NO:69-106, wherein said degenerate nucleotide sequence encodes the same amino acid sequence as any of SEQ ID NO:1-40, 42, 43, 45-48, 50, 51, 52, 54, 56, 58-64, 66, or 67.

Preferred pesticidal proteins of the present invention are encoded by a nucleotide sequence sufficiently identical to the nucleotide sequence of any of SEQ ID NO:69-106, or the pesticidal proteins are sufficiently identical to the amino acid sequence set forth in any of SEQ ID NO:1-40, 42, 43, 45-48, 50, 51, 52, 54, 56, 58-64, 66, or 67. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO: 1-40, 42, 43, 45-48, 50, 51, 52, 54, 56, 58-64, 66, 67, or 69-106). The percent identity between two sequences can be determined using techniques similar to those described below, with or without allowing gaps. In calculating percent identity, typically exact matches are counted. A gap, i.e. a position in an alignment where a residue is present in one sequence but not in the other, is regarded as a position with non-identical residues.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485;

Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention (e.g., at least about 70%, at least about 75%, 80%, 85%, 90%, 95% or more sequence identity across the entirety of the reference sequence) and having or conferring pesticidal activity. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism or sample by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Thus, the present invention encompasses probes for hybridization, as well as nucleotide sequences capable of hybridization to all or a portion of a nucleotide sequence of the invention (e.g., at least about 10, 25, 50, 100, 150, 200, 250, 300, 350, 400, 450, 500, or up to the full length of a nucleotide sequence disclosed herein). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138:267-284: $T_m$=81.5° C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in any of SEQ ID NO:1-40, 42, 43, 45-48, 50, 51, 52, 54, 56, 58-64, 66, or 67. Fragments, biologically active portions, and variants thereof are also provided, and may be used to practice the methods of the present invention. An "isolated protein" or a "recombinant protein" is used to refer to a protein that is no longer in its natural environment, for example in vitro or in a recombinant bacterial or plant host cell. In some embodiments, the recombinant protein is a variant of any of SEQ ID NO:1-40, 42, 43, 45-48, 50, 51, 52, 54, 56, 58-64, 66, or 67, wherein the variant comprises at least one amino acid substitution, deletion, or insertion relative to any of SEQ ID NO:1-40, 42, 43, 45-48, 50, 51, 52, 54, 56, 58-64, 66, or 67.

"Fragments" or "biologically active portions" include polypeptide fragments comprising amino acid sequences sufficiently identical to the amino acid sequence set forth in any of SEQ ID NO:1-40, 42, 43, 45-48, 50, 51, 52, 54, 56, 58-64, 66, or 67, and that exhibit pesticidal activity. A biologically active portion of a pesticidal protein can be a polypeptide that is, for example, 10, 25, 50, 100, 150, 200, 250, or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of any of SEQ ID NO:1-40, 42, 43, 45-48, 50, 51, 52, 54, 56, 58-64, 66, or 67. The invention encompasses other fragments, however, such as any fragment in the protein greater than about 10, 20, 30, 50, 100, 150, 200, 250 or more amino acids in length.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:1-40, 42, 43, 45-48, 50, 51, 52, 54, 56, 58-64, 66, or 67. Variants also include polypeptides encoded by a nucleic acid molecule that hybridizes to the nucleic acid molecule of any of SEQ ID NO:69-106, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

In various embodiments of the present invention, pesticidal proteins include amino acid sequences deduced from the full-length nucleotide sequences disclosed herein, and amino acid sequences that are shorter than the full-length sequences due to the use of an alternate downstream start site. Thus, the nucleotide sequence of the invention and/or vectors, host cells, and plants comprising the nucleotide sequence of the invention (and methods of making and using the nucleotide sequence of the invention) may comprise a nucleotide sequence encoding the amino acid sequence corresponding to any of SEQ ID NO:1-40, 42, 43, 45-48, 50, 51, 52, 54, 56, 58-64, 66, or 67.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Thus, one aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in any of SEQ ID NO:1-40, 42, 43, 45-48, 50, 51, 52, 54, 56, 58-64, 66, or 67 or a fragment thereof. In another embodiment, the antibody specifically binds to a fusion protein comprising an amino acid sequence selected from the amino acid sequence set forth in any of SEQ ID NO:1-40, 42, 43, 45-48, 50, 51, 52, 54, 56, 58-64, 66, or 67 or a fragment thereof. In various embodiments, the antibody that specifically binds to the protein of the invention or a fusion protein comprising the protein of the invention is a non-naturally occurring antibody.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

The antibodies of the invention may be contained within a kit useful for detection of the protein or peptide molecules of the invention. The invention further comprises a method of detecting the protein or peptide molecule of the invention (particularly a protein encoded by the amino acid sequence set forth in any of SEQ ID NO:1-40, 42, 43, 45-48, 50, 51, 52, 54, 56, 58-64, 66, or 67, including variants or fragments thereof that are capable of specifically binding to the antibody of the invention) comprising contacting a sample with the antibody of the invention and determining whether the sample contains the protein or peptide molecule of the invention. Methods for utilizing antibodies for the detection of a protein or peptide of interest are known in the art.

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of any of SEQ ID NO:1-40, 42, 43, 45-48, 50, 51, 52, 54, 56, 58-64, 66, or 67, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays or the toxin is exposed directly to the insect. See, for example Marrone et al. (1985) *J. of Economic Entomology* 78:290-293 and Cira et al. (2017) *J Pest Sci* 90:1257-1268. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

In yet another embodiment, variant nucleotide and/or amino acid sequences can be obtained using one or more of error-prone PCR, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis, permutational mutagenesis, synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and the like.

Vectors

A pesticidal sequence of the invention may be provided in an expression cassette for expression in a host cell of interest, e.g. a plant cell or a microbe. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Thus, further provided herein is a polypeptide comprising an amino acid sequence of the present invention that is operably linked to a heterologous leader or signal sequence.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and/or 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In some embodiments, the nucleotide sequence is operably linked to a heterologous promoter capable of directing expression of said nucleotide sequence in a host cell, such as a microbial host cell or a plant host cell. The cassette may additionally contain at least one additional gene to be cotransformed into the organism. Alternatively, the additional gene(s) can be provided on multiple expression cassettes.

In various embodiments, the nucleotide sequence of the invention is operably linked to a heterologous promoter capable of directing expression of the nucleotide sequence in a cell, e.g., in a plant cell or a microbe. "Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Natl. Acad. Sci. USA,* 76:760-764. Many suitable promoters for use in plants are well known in the art.

For instance, suitable constitutive promoters for use in plants include: the promoters from plant viruses, such as the peanut chlorotic streak caulimovirus (PCISV) promoter (U.S. Pat. No. 5,850,019); the 35S promoter from cauliflower mosaic virus (CaMV) (Odell et al. (1985) *Nature* 313:810-812); the 35S promoter described in Kay et al. (1987) *Science* 236: 1299-1302; promoters of *Chlorella* virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171 and U.S. Pat. No. 5,641,876); ubiquitin (Christensen et al. (1989) *Plant Mol. Biol.* 12:619-632 and Christensen et al. (1992) *Plant Mol. Biol.* 18:675-689) and Grefen et al. (2010) *Plant J,* 64:355-365; pEMU (Last et al. (1991) *Theor. Appl. Genet.* 81:581-588); MAS (Velten et al. (1984) *EMBO J.* 3:2723-2730 and U.S. Pat. No. 5,510,474); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO97/41228); a plant ribulose-biscarboxylase/oxygenase (RuBisCO) small subunit gene; the circovirus (AU 689 311) or the Cassava vein mosaic virus (CsVMV, U.S. Pat. No. 7,053,205); promoters from soybean (Pbdc6 or Pbdc7, described in WO/2014/150449 or ubiquitin 3 promoter described in U.S. Pat. Nos. 7,393,948 and 8,395,021); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) *PNAS* 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243:32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.,* 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

In one embodiment of this invention, a promoter sequence specific for particular regions or tissues of plants can be used to express the pesticidal proteins of the invention, such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO92/17580), the albumin promoter (WO98/45460), the oleosin promoter (WO98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO98/45445). Multiple promoters can be used in the constructs of the invention, including in succession.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PCISV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156); the translation activator of the tobacco mosaic virus (TMV) described in Application WO87/07644, or of the tobacco etch virus (TEV) described by Carrington & Freed 1990, J. Virol. 64: 1590-1597, for example, or introns such as the adh1 intron of maize or intron 1 of rice actin. See also PCT WO96/23898, WO2012/021794, WO2012/021797, WO2011/084370, and WO2011/028914.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell (synthetic DNA sequence). That is, the genes can be synthesized using host cell-preferred codons for improved expression, or may be synthesized using codons at a host-preferred codon usage frequency. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, U.S. Patent Publication No. 20090137409, and Murray et al. (1989) *Nucleic Acids Res.* 17:477-498, herein incorporated by reference.

It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Thus, in one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In some embodiments, the protein or nucleotide sequence of the invention is advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides, and others which confer tolerance to certain insects, those which confer tolerance to certain diseases, DNAs that encodes RNAs that provide nematode or insect control, and the like. Such genes are in particular described in published PCT Patent Applications WO91/02071 and WO95/06128 and in U.S. Pat. No. 7,923,602 and US Patent Application Publication No. 20100166723, each of which is herein incorporated by reference in its entirety.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769,061, 5,094,945, 4,940,835, 5,188,642, 4,971,908, 5,145,783, 5,310,667, 5,312,910, 5,627,061, 5,633,435), a gene encoding glyphosate-n-acetyltransferase (for example, U.S. Pat. Nos. 8,222,489, 8,088,972, 8,044,261, 8,021,857, 8,008,547, 7,999,152, 7,998,703, 7,863,503, 7,714,188, 7,709,702, 7,666,644, 7,666,643, 7,531,339, 7,527,955, and 7,405,074), a gene encoding glyphosate oxydoreductase (for example, U.S. Pat. No. 5,463,175), or a gene encoding an HPPD inhibitor-tolerant protein (for example, the HPPD inhibitor tolerance genes described in WO 2004/055191, WO 199638567, U.S. Pat. No. 6,791,014, WO2011/068567, WO2011/076345, WO2011/085221, WO2011/094205, WO2011/068567, WO2011/094199, WO2011/094205, WO2011/145015, WO2012/056401, and WO2014/043435).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO2004/074443), and which is described in Patent Application U.S. Pat. No. 6,566,587, hereinafter named double mutant maize EPSPS or 2mEPSPS, or the gene which encodes an EPSPS isolated from *Agrobacterium* and which is described by sequence ID No. 2 and sequence ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACE3, particularly the mutants or variants of GRG23 as described in WO2008/100353, such as GRG23 (ace3)R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. No. 5,510,471 or 5,633,448.

Exemplary herbicide tolerance traits that can be combined with the nucleic acid sequence of the invention further include at least one ALS (acetolactate synthase) inhibitor (WO2007/024782); a mutated *Arabidopsis* ALS/AHAS gene (U.S. Pat. No. 6,855,533); genes encoding 2,4-D-monooxygenases conferring tolerance to 2,4-D (2,4-dichlorophenoxyacetic acid) by metabolization (U.S. Pat. No. 6,153,401); and, genes encoding Dicamba monooxygenases conferring tolerance to dicamba (3,6-dichloro-2-methoxybenzoic acid) by metabolization (US 2008/0119361 and US 2008/0120739).

In various embodiments, the nucleic acid of the invention is stacked with one or more herbicide tolerant genes, including one or more HPPD inhibitor herbicide tolerant genes, and/or one or more genes tolerant to glyphosate and/or glufosinate.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO97/17432 & WO98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1A-Cry1F proteins described in U.S. Pat. Nos. 6,326,169; 6,281,016; 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO2002/057664 or toxic fragments thereof, the Cry1A.105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT202 or COT203 cotton events (WO2005/054479 and WO2005/054480, respectively), the Cry proteins as described in WO2001/47952, the VIP3Aa protein or a toxic fragment thereof as described in Estruch et al. (1996), Proc Natl Acad Sci USA. 28; 93(11):5389-94 and U.S. Pat. No. 6,291,156, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932 (e.g., Waterfield et al., 2001, Appl Environ Microbiol. 67(11):5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

In various embodiments, the nucleic acid of the invention can be combined in plants with one or more genes conferring a desirable trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like.

Particularly useful transgenic events which may be combined with the genes of the current invention in plants of the same species (e.g., by crossing or by re-transforming a plant containing another transgenic event with a chimeric gene of the invention), include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA- 2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480);); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-1 (brinjal, insect control, not deposited, described in WO 07/091277); Event FI117 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603

(corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No. PTA-11041) optionally stacked with event EE-GM1/LL27 or event EE-GM2/LL55 (WO2011/063413A2), event DAS-68416-4 (soybean, herbicide tolerance, ATCC Accession No. PTA-10442, WO2011/066360A1), event DAS-68416-4 (soybean, herbicide tolerance, ATCC Accession No. PTA-10442, WO2011/066384A1), event DP-040416-8 (corn, insect control, ATCC Accession No. PTA-11508, WO2011/075593A1), event DP-043A47-3 (corn, insect control, ATCC Accession No. PTA-11509, WO2011/075595A1), event DP-004114-3 (corn, insect control, ATCC Accession No. PTA-11506, WO2011/084621A1), event DP-032316-8 (corn, insect control, ATCC Accession No. PTA-11507, WO2011/084632A1), event MON-88302-9 (oilseed rape, herbicide tolerance, ATCC Accession No. PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No. PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No. PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No. PTA-11993, WO2013/010094A1), event MZDT09Y (corn, ATCC Accession No. PTA-13025, WO2013/012775A1).

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol.*

*Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Pesticidal Control

General methods for employing strains comprising a nucleotide sequence of the present invention, or a variant thereof, in pest control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene of the invention and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of the target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, hemipteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. For example, the pesticide may result in reduced egg hatching, mortality at any stage of development of the insect, reduced molting, and/or reduced feeding of the pest on a target organisms (e.g., reduced number of feeding sites a plant or plant cell and/or reduced damage to a plant or plant cell). This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, the crystal and/or the spore suspension, or the isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Hemipteran pests (which include species that are designated as *Hemiptera, Homoptera*, or Heteroptera) include, but are not limited to, *Lygus* spp., such as Western tarnished plant bug (*Lygus hesperus*), the tarnished plant bug (*Lygus lineolaris*), and green plant bug (*Lygus elisus*); aphids, such as the green peach aphid (*Myzus persicae*), cotton aphid (*Aphis gossypii*), cherry aphid or black cherry aphid (*Myzus cerasi*), soybean aphid (*Aphis glycines Matsumura*); brown plant hopper (*Nilaparvata lugens*), and rice green leafhopper (*Nephotettix* spp.); and stink bugs, such as green stink bug (*Acrosternum hilare*), brown marmorated stink bug (*Halyomorpha halys*), southern green stink bug (*Nezara viridula*), rice stink bug (*Oebalus pugnax*), forest bug (*Pentatoma rufipes*), European stink bug (*Rhaphigaster nebulosa*), and the shield bug *Troilus luridus*.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Spodoptera cosmioides; Spodoptera eridania; Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; zygogramma exclamationis, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Spodoptera cosmioides; Spodoptera eridania; Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; *Chilu suppressalis*, Asiatic rice borer; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Spodoptera cosmioides; Spodoptera eridania; Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Euschistus heros*, neotropical brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, Bacillus thuriengiensis, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid; Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin; Cereals Herbicides: 2.4-D, Amidosulfuron, Bromoxynil, Carfentrazone-E, Chlorotoluron, Chlorsulfuron, Clodinafop-P, Clopyralid, Dicamba, Diclofop-M, Diflufenican, Fenoxaprop, Florasulam, Flucarbazone-NA, Flufenacet, Flupyrosulfuron-M, Fluroxypyr, Flurtamone, Glyphosate, lodosulfuron, loxynil, Isoproturon, MCPA, Mesosulfuron, Metsulfuron, Pendimethalin, Pinoxaden, Propoxycarbazone, Prosulfocarb, Pyroxsulam, Sulfosulfuron, Thifensulfuron, Tralkoxydim, Triasulfuron, Tribenuron, Trifluralin, Tritosulfuron; Cereals Fungicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluopyram, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin; Cereals Insecticides: Dimethoate, Lambda-cyhalthrin, Deltamethrin, alpha-Cypermethrin, ß-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, ß-Cyfluthrin, Cypermethrin, Bifenthrin, Lufenuron, Tebupirimphos, Ethiprole, Cyazypyr, Thiacloprid, Acetamiprid, Dinetofuran, Avermectin; Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Etofenprox, Carbofuran, Benfuracarb, Sulfoxaflor; Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, ß-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, ß-Cyfluthrin, gamma/lambda Cyhalothrin, 4-[[(6-Chlorpyridin-3-yl)methyl](2,2-difluorethyl)amino]furan-2 (5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluxapyroxad, Iprodione, Isopyrazam, Mepiquat-chloride, Metconazole, Metominostrobin, Paclobutrazole, Penthiopyrad, Picoxystrobin, Prochloraz, Prothioconazole, Pyraclostrobin, Tebuconazole, Thiophanate-methyl, Trifloxystrobin, Vinclozolin; Canola Insecticides: Carbofuran, Thiacloprid, Deltamethrin, Imidacloprid, Clothianidin, Thiamethoxam, Acetamiprid, Dinetofuran, ß-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2, 2-difluorethyl)amino]furan-2(5H)-on.

Methods of Introducing Gene of the Invention into Another Plant

Also provided herein are methods of introducing the nucleic acid of the invention into another plant. The nucleic acid of the invention, or a fragment thereof, can be introduced into second plant by recurrent selection, backcrossing, pedigree breeding, line selection, mass selection, mutation breeding and/or genetic marker enhanced selection.

Thus, in one embodiment, the methods of the invention comprise crossing a first plant comprising a nucleic acid of the invention with a second plant to produce F1 progeny plants and selecting F1 progeny plants that comprise the nucleic acid of the invention. The methods may further comprise crossing the selected progeny plants with the first plant comprising the nucleic acid of the invention to produce backcross progeny plants and selecting backcross progeny plants that comprise the nucleic acid of the invention. Methods for evaluating pesticidal activity are provided elsewhere herein. The methods may further comprise repeating these steps one or more times in succession to produce selected second or higher backcross progeny plants that comprise the nucleic acid of the invention.

Any breeding method involving selection of plants for the desired phenotype can be used in the method of the present invention. In some embodiments, The F1 plants may be self-pollinated to produce a segregating F2 generation. Individual plants may then be selected which represent the desired phenotype (e.g., pesticidal activity) in each generation (F3, F4, F5, etc.) until the traits are homozygous or fixed within a breeding population.

The second plant can be a plant having a desired trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like. The second plant may be an elite event as described elsewhere herein In various embodiments, plant parts (whole plants, plant organs (e.g., leaves, stems, roots, etc.), seeds, plant cells, propagules, embryos, and the like) can be harvested from the resulting cross and either propagated or collected for downstream use (such as food, feed, biofuel, oil, flour, meal, etc).

Methods of Obtaining a Plant Product

The present invention also relates to a process for obtaining a commodity product, comprising harvesting and/or milling the grains from a crop comprising a nucleic acid of the invention to obtain the commodity product. Agronomically and commercially important products and/or compositions of matter including but not limited to animal feed, commodities, and plant products and by-products that are intended for use as food for human consumption or for use in compositions and commodities that are intended for human consumption, particularly devitalized seed/grain products, including a (semi-)processed products produced from such grain/seeds, wherein said product is or comprises whole or processed seeds or grain, animal feed, corn or soy meal, corn or soy flour, corn, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans (raw, roasted, or as edamame), soy yogurt, soy cheese, tofu, yuba, as well as cooked, polished, steamed, baked or parboiled grain, and the like are intended to be within the scope of the present invention if these products and compositions of matter contain detectable amounts of the nucleotide and/or amino acid sequences set forth herein as being diagnostic for any plant containing such nucleotide sequences.

The following examples are offered by way of illustration and not by way of limitation.

EXPERIMENTAL EXAMPLES

Example 1. Discovery of Novel Pesticidal Genes

Novel pesticidal genes were identified from a *Bacillus cereus* strain using the following steps:
Sequencing of the fragmented DNA by high-throughput pyrosequencing methods.
Identification of putative toxin genes via homology and/or other computational analyses.

TABLE 1

| | bp005 genes identified | | | |
|---|---|---|---|---|
| Gene name | Molecular weight (kD) | Closest homolog | Nucleotide SEQ ID NO | Amino acid SEQ ID NO |
| bp005 | 19.7 | 99% YvgO | 69 | 1 |
| bp005(trun) | | | | 2 |
| bp005v04 | | | 70 | 3 |
| bp005v06 | | | 71 | 4 |

Bp005 was synthesized and cloned into the His-tagged vector to create plasmid pGHis-bp005. The clone was confirmed by sequencing and pGHis-bp005 was transformed in B121 competent cells. A single colony was inoculated in LB media and grown at 37° C. until log phase, and induced with 0.5 mM IPTG at 20° C. for 16 hours. Purified BP005 was submitted to bioassay vs. hemipteran pests according to standard protocol. Bp005 was active against *Nezara viridula* (75% mortality).

Homologs of bp005 were identified from the bacterial strains listed in Table 2. The homologs were also submitted to bioassay vs. *Nezara viridula* according to standard protocols. The results of the bioassays are shown in Table 2.

TABLE 2

| | Activity of homologs of bp005 against *Nezara viridula* | | | | | |
|---|---|---|---|---|---|---|
| Gene name | Source Strain Species | AA SEQ ID NO | Nt SEQ ID NO | Homology (% identity) relative to bp005v04 (SEQ ID NO: 3) | Percent Mortality against *Nezara viridula* | Percent Molting |
| Axmi2042(v02) | *Bacillus cereus* | 6 | 73 | 87 | 97% | 0% |
| Axmi2054(v02) | *Bacillus cereus* | 8 | 75 | 86 | 59% | 0% |
| Axmi2147(v01) | *Bacillus cytotoxicus* | 9 | 76 | 91 | Not tested or inconclusive | Not tested or inconclusive |
| Axmi2148(v01) | *Bacillus cereus* | 10 | 77 | 92 | Not tested or inconclusive | Not tested or inconclusive |

TABLE 2-continued

Activity of homologs of bp005 against *Nezara viridula*

| Gene name | Source Strain Species | AA SEQ ID NO | Nt SEQ ID NO | Homology (% identity) relative to bp005v04 (SEQ ID NO: 3) | Percent Mortality against *Nezara viridula* | Percent Molting |
|---|---|---|---|---|---|---|
| Axmi2149(v01) | *Bacillus cytotoxicus* | 11 | 78 | 91 | Not tested or inconclusive | Not tested or inconclusive |
| Axmi2150(v01) | *Bacillus pumilus* | 12 | 79 | 95 | Not tested or inconclusive | Not tested or inconclusive |
| Axmi2151(v01) | *Bacillus thuringiensis* | 13 | 80 | 93 | Not tested or inconclusive | Not tested or inconclusive |
| Axmi2152(v01) | *Bacillus cytotoxicus* | 14 | 81 | 92 | Not tested or inconclusive | Not tested or inconclusive |
| Axmi2153(v01) | *Bacillus thuringiensis* | 15 | 82 | 92 | Not tested or inconclusive | Not tested or inconclusive |
| Axmi2154(v01) | *Bacillus thuringiensis* | 16 | 83 | 91 | 71% | 0% |
| Axmi2155(v01) | *Bacillus weihenstephanensis* | 17 | 84 | 88 | Not tested or inconclusive | Not tested or inconclusive |
| Axmi2156(v01) | *Bacillus thuringiensis* | 18 | 85 | 91 | Not tested or inconclusive | Not tested or inconclusive |
| Axmi2157(v01) | *Bacillus cytotoxicus* | 19 | 86 | 92 | Not tested or inconclusive | Not tested or inconclusive |
| Axmi2158(v01) | *Bacillus cytotoxicus* | 20 | 87 | 93 | Not tested or inconclusive | Not tested or inconclusive |
| Axmi2159(v01) | *Bacillus thuringiensis* | 21 | 88 | 95 | Not tested or inconclusive | Not tested or inconclusive |
| Axmi2160(v01) | *Bacillus weihenstephanensis* | 22 | 89 | 92 | Not tested or inconclusive | Not tested or inconclusive |
| Axmi2161(v01) | *Bacillus weihenstephanensis* | 23 | 90 | 91 | Not tested or inconclusive | Not tested or inconclusive |
| Axmi2162(v01) | *Bacillus cereus* | 24 | 91 | 85 | 50% | 0% |
| Axmi2163(v01) | *Bacillus thuringiensis* | 25 | 92 | 91 | 50% | 0% |
| Axmi2164(v01) | *Bacillus thuringiensis* | 26 | 93 | 93 | Not tested or inconclusive | Not tested or inconclusive |
| Axmi2165(v01) | *Bacillus thuringiensis* | 27 | 94 | 90 | Not tested or inconclusive | Not tested or inconclusive |
| Axmi2166(v01) | *Bacillus thuringiensis* | 28 | 95 | 92 | Not tested or inconclusive | Not tested or inconclusive |
| Axmi2167(v01) | *Bacillus thuringiensis* | 29 | 96 | 93 | Not tested or inconclusive | Not tested or inconclusive |
| Axmi2168(v01) | *Bacillus cereus* | 30 | 97 | 86 | Not tested or inconclusive | Not tested or inconclusive |
| Axmi2169(v01) | *Bacillus thuringiensis* | 31 | 98 | 94 | Not tested or inconclusive | Not tested or inconclusive |
| Axmi2170(v01) | *Bacillus thuringiensis* | 32 | 99 | 90 | Not tested or inconclusive | Not tested or inconclusive |
| Axmi2171(v01) | *Bacillus thuringiensis* | 33 | 100 | 89 | Not tested or inconclusive | Not tested or inconclusive |
| Axmi2172(v01) | *Bacillus cytotoxicus* | 34 | 101 | 91 | Not tested or inconclusive | Not tested or inconclusive |

TABLE 2-continued

Activity of homologs of bp005 against *Nezara viridula*

| Gene name | Source Strain Species | AA SEQ ID NO | Nt SEQ ID NO | Homology (% identity) relative to bp005v04 (SEQ ID NO: 3) | Percent Mortality against *Nezara viridula* | Percent Molting |
|---|---|---|---|---|---|---|
| Axmi2173(v01) | *Bacillus thuringiensis* | 35 | 102 | 95 | Not tested or inconclusive | Not tested or inconclusive |
| Axmi2174(v01) | *Bacillus thuringiensis* | 36 | 103 | 95 | Not tested or inconclusive | Not tested or inconclusive |
| Axmi2175(v01) | *Bacillus thuringiensis* | 37 | 104 | 91 | Not tested or inconclusive | Not tested or inconclusive |
| Axmi2176(v01) | *Bacillus pumilus* | 38 | 105 | 90 | Not tested or inconclusive | Not tested or inconclusive |

To elucidate potential amino acid residues which may be critical for the function of bp005, a series of mutations was made in bp005v04 (SEQ ID NO:3) and tested against *Nezara viridula*. The bioassay results are shown in Table 3.

TABLE 3

Activity of mutants of bp005 against *Nezara viridula*

| Mutant ID | Amino Acid SEQ ID NO: | Percent Mortality against *Nezara viridula* | Percent Molting |
|---|---|---|---|
| bp004v04 (control) | 3 | 17% | 0% |
| A15G | 39 | Not tested or inconclusive | Not tested or inconclusive |
| D6S | 40 | 29% | 0% |
| D74H | 41 | Not active | Not active |
| D85S | 42 | 25% | 0% |
| Dec (L5F, S29P, V35M, R46K, N55A, R61H, N63R, Y73L, I97D, H111Y) | 43 | Not tested or inconclusive | Not tested or inconclusive |
| E87Q | 44 | Not active | Not active |
| H111Y | 45 | Not tested or inconclusive | Not tested or inconclusive |
| I97D | 46 | Not tested or inconclusive | Not tested or inconclusive |
| K113E | 47 | Not tested or inconclusive | Not tested or inconclusive |
| L5F | 48 | Not tested or inconclusive | Not tested or inconclusive |
| N23K | 49 | Not active | Not active |
| N55A | 50 | 46% | 0% |
| N57G | 51 | 50% | 0% |
| N63R | 52 | Not tested or inconclusive | Not tested or inconclusive |
| Oct (D6S, A15G, V35C, N57G, V72N, D74H, D85S, E87Q) | 53 | Not active | Not active |
| Quad (R19A, N23K, T26Q, K113E) | 54 | Not tested or inconclusive | Not tested or inconclusive |
| Quad1 (L5F, V35M, Y73L, I97D) | 55 | Not active | Not active |
| Quad2 (S29P, R46K, N55A, H111Y) | 56 | 88% | 0% |
| Quint (D6S, A15G, V35C, D74H, D85S) | 57 | Not active | Not active |
| R19A | 58 | Not tested or inconclusive | Not tested or inconclusive |
| R46K | 59 | Not tested or inconclusive | Not tested or inconclusive |
| R61H | 60 | Not tested or inconclusive | Not tested or inconclusive |
| S29P | 61 | Not tested or inconclusive | Not tested or inconclusive |

TABLE 3-continued

Activity of mutants of bp005 against *Nezara viridula*

| Mutant ID | Amino Acid SEQ ID NO: | Percent Mortality against *Nezara viridula* | Percent Molting |
|---|---|---|---|
| T26Q | 62 | Not tested or inconclusive | Not tested or inconclusive |
| Tri (N57G, V72N, E87Q) | 63 | 58% | 0% |
| V35C | 64 | Not tested or inconclusive | Not tested or inconclusive |
| V35M | 65 | Not active | Not active |
| V72N | 66 | 58% | 0% |
| Y73L | 67 | 42% | 4% |

Example 2. Analysis of Amino Acid Composition of Homologs and Variants of Bp005

A computational analysis was performed to identify potentially critical motifs that may be able to distinguish active from inactive bp005 homologs. The confirmed active and inactive sequences were initially aligned using MEGA. The sequences were then split into trigrams of amino acids (that is, a sliding window of groups of three amino acids), and then encoded into indices. The encoded sequences and their activity information were then used to build a decision tree classifier. The sequence positions identified by the classifier as the most significant in the classification were then listed, and the critical trigrams appearing in those locations were identified. The most significant trigram in this analysis was the trigram corresponding to positions 35-37 of bp005v04.

A comparison of the amino acid sequences of all homologs that were active against *Nezara viridula* was performed and residues which appear in 95% of the homologs having at least 90% sequence identity to bp005v04 are noted in Table 4. An "X" in column 2 of Table 4 suggests that the amino acid at that position is variable amongst the homologs.

TABLE 4

Composition of bp005 homologs

| Amino acid position relative to bp005v04 | Amino Acid |
|---|---|
| 1 | M |
| 2 | S |
| 3 | A |
| 4 | N |
| 5 | L |
| 6 | X |
| 7 | V |
| 8 | X |
| 9 | X |
| 10 | D |
| 11 | V |
| 12 | L |
| 13 | G |
| 14 | I |
| 15 | A |
| 16 | N |
| 17 | X |
| 18 | I |
| 19 | R |
| 20 | B |
| 21 | A |
| 22 | I |
| 23 | N |
| 24 | X |
| 25 | Q |
| 26 | T |

TABLE 4-continued

Composition of bp005 homologs

| Amino acid position relative to bp005v04 | Amino Acid |
|---|---|
| 27 | N |
| 28 | R |
| 29 | X |
| 30 | G |
| 31 | F |
| 32 | V |
| 33 | K |
| 34 | G |
| 35 | V |
| 36 | M |
| 37 | E |
| 38 | S |
| 39 | T |
| 40 | F |
| 41 | Y |
| 42 | X |
| 43 | A |
| 44 | G |
| 45 | Q |
| 46 | X |
| 47 | Y |
| 48 | N |
| 49 | V |
| 50 | M |
| 51 | V |
| 52 | F |
| 53 | N |
| 54 | L |
| 55 | X |
| 56 | Q |
| 57 | X |
| 58 | Y |
| 59 | Z |
| 60 | D |
| 61 | R |
| 62 | F |
| 63 | N |
| 64 | G |
| 65 | V |
| 66 | K |
| 67 | F |
| 68 | F |
| 69 | G |
| 70 | T |
| 71 | T |
| 72 | X |
| 73 | X |
| 74 | D |
| 75 | G |
| 76 | I |
| 77 | T |
| 78 | F |
| 79 | G |
| 80 | I |
| 81 | W |
| 82 | V |
| 83 | F |

TABLE 4-continued

Composition of bp005 homologs

| Amino acid position relative to bp005v04 | Amino Acid |
|---|---|
| 84 | E |
| 85 | X |
| 86 | G |
| 87 | Z |
| 88 | F |
| 89 | T |
| 90 | N |
| 91 | X |
| 92 | G |
| 93 | D |
| 94 | G |
| 95 | G |
| 96 | W |
| 97 | I |
| 98 | N |
| 99 | W |
| 100 | A |
| 101 | F |
| 102 | R |
| 103 | G |
| 104 | W |
| 105 | F |
| 106 | D |
| 107 | R |
| 108 | B |
| 109 | G |
| 110 | G |
| 111 | X |
| 112 | V |
| 113 | K |
| 114 | F |
| 115 | Y |
| 116 | R |
| 117 | X |

Example 3. Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, and then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests and Journal of Economic Entomology* or by discussion with members of the Entomological Society of America (ESA).

In some embodiments, the DNA regions encoding the toxin region of the pesticidal proteins disclosed herein are cloned into the *E. coli* expression vector pMAL-C4x behind the malE gene coding for Maltose binding protein (MBP). These in-frame fusions result in MBP-bp005 fusion proteins expression in *E. coli*.

For expression in *E. coli*, BL21*DE3 are transformed with individual plasmids. Single colonies are inoculated in LB supplemented with carbenicillin and glucose, and grown overnight at 37° C. The following day, fresh medium is inoculated with 1% of overnight culture and grown at 37° C. to logarithmic phase. Subsequently, cultures are induced with 0.3 mM IPTG overnight at 20° C. Each cell pellet is suspended in 20 mM Tris-Cl buffer, pH 7.4+200 mM NaCl+1 mM DTT+protease inhibitors and sonicated. Analysis by SDS-PAGE can be used to confirm expression of the fusion proteins.

Total cell free extracts are then run over amylose column attached to fast protein liquid chromatography (FPLC) for affinity purification of MBP-bp005 fusion proteins. Bound fusion proteins are eluted from the resin with 10 mM maltose solution. Purified fusion proteins are then cleaved with either Factor Xa or trypsin to remove the amino terminal MBP tag from the BP005 protein. Cleavage and solubility of the proteins can be determined by SDS-PAGE

Example 4. Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

In one aspect of the invention, synthetic DNA sequences are designed and generated. These synthetic sequences have altered nucleotide sequence relative to the parent sequence, but encode proteins that are essentially identical to the parent sequence.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:68) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL (SEQ ID NO:68) sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 5. Soybean Transformation

Soybean transformation is achieved using methods well known in the art, such as the one described using the *Agrobacterium tumefaciens* mediated transformation soybean half-seed explants using essentially the method described by Paz et al. (2006), Plant cell Rep. 25:206. Transformants are identified using tembotrione as selection marker. The appearance of green shoots was observed, and documented as an indicator of tolerance to the herbicide isoxaflutole or tembotrione. The tolerant transgenic shoots will show normal greening comparable to wild-type soybean shoots not treated with isoxaflutole or tembotrione, whereas wild-type soybean shoots treated with the same amount of isoxaflutole or tembotrione will be entirely bleached. This indicates that the presence of the HPPD protein enables the tolerance to HPPD inhibitor herbicides, like isoxaflutole or tembotrione.

Tolerant green shoots are transferred to rooting media or grafted. Rooted plantlets are transferred to the greenhouse after an acclimation period. Plants containing the transgene are then sprayed with HPPD inhibitor herbicides, as for example with tembotrione at a rate of 100 g AI/ha or with mesotrione at a rate of 300 g AI/ha supplemented with ammonium sulfate methyl ester rapeseed oil. Ten days after the application the symptoms due to the application of the herbicide are evaluated and compared to the symptoms observed on wild type plants under the same conditions.

Example 6: Cotton T0 Plant Establishment and Selection

Cotton transformation is achieved using methods well known in the art, especially preferred method in the one described in the PCT patent publication WO 00/71733. Regenerated plants are transferred to the greenhouse. Following an acclimation period, sufficiently grown plants are sprayed with HPPD inhibitor herbicides as for example tembotrione equivalent to 100 or 200 gAI/ha supplemented with ammonium sulfate and methyl ester rapeseed oil. Seven days after the spray application, the symptoms due to the treatment with the herbicide are evaluated and compared to the symptoms observed on wild type cotton plants subjected to the same treatment under the same conditions.

Example 7. Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 8. Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (22° C. in the dark). After co-cultivation, explants are transferred to recovery period media for 5-10 days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

Example 9. Transformation of Rice

Immature rice seeds, containing embryos at the right developmental stage, are collected from donor plants grown under well controlled conditions in the greenhouse. After sterilization of the seeds, immature embryos are excised and preinduced on a solid medium for 3 days. After preinduction, embryos are immersed for several minutes in a suspension of *Agrobacterium* harboring the desired vectors. Then embryos are cocultivated on a solid medium containing acetosyringone and incubated in the dark for 4 days. Explants are then transferred to a first selective medium containing phosphinotricin as selective agent. After approximately 3 weeks, scutella with calli developing were cut into several smaller pieces and transferred to the same selective medium. Subsequent subcultures are performed approximately every 2 weeks. Upon each subculture, actively growing calli are cut into smaller pieces and incubated on a second selective medium. After several weeks calli clearly resistant to phosphinotricin are transferred to a selective regeneration medium. Plantlets generated are cultured on half strength MS for full elongation. The plants are eventually transferred to soil and grown in the greenhouse.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant nucleic acid molecule comprising a nucleotide sequence encoding an amino acid sequence having pesticidal activity, wherein said nucleotide sequence is:

a) the nucleotide sequence set forth in any of SEQ ID NO: 69-75, 83, 91, 92, 96-105 or 106;

b) a nucleotide sequence that encodes a polypeptide comprising the amino acid sequence of any of SEQ ID NO: 1-8, 16, 24-25, 29-40, 42, 50-51, 56 or 63;

c) a nucleotide sequence that encodes a polypeptide comprising an amino acid sequence having at least 85% sequence identity to the amino acid sequence of any of SEQ ID NO: 5 or 7;

d) a nucleotide sequence that encodes a polypeptide comprising an amino acid sequence having at least 90% sequence identity to the amino acid sequence of any of SEQ ID NO: 6, 8, 24, or 30;

e) a nucleotide sequence that encodes a polypeptide comprising an amino acid sequence having at least 95% sequence identity to the amino acid sequence of any of SEQ ID NO: 16, 25, 29, 31-34, 37, or 38; or f) a nucleotide sequence that encodes a polypeptide comprising an amino acid sequence having at least 98% sequence identity to the amino acid sequence of any of SEQ ID NO: 35, 36, 56 or 63; and wherein said nucleotide sequence is operably linked to a heterologous promoter.

2. The recombinant nucleic acid molecule of claim 1, wherein said nucleotide sequence is a synthetic sequence that has been designed for expression in a plant.

3. The recombinant nucleic acid molecule of claim 1, wherein said heterologous promoter is capable of directing expression of said nucleotide sequence in a plant cell.

4. A vector comprising the recombinant nucleic acid molecule of claim 1.

5. The vector of claim 4, further comprising a nucleic acid molecule encoding a heterologous polypeptide.

6. A host cell that contains the recombinant nucleic acid of claim 1.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the nucleic acid molecule of claim 1.

12. A recombinant polypeptide comprising a polypeptide with pesticidal activity, wherein the polypeptide is:
　a) a polypeptide comprising the amino acid sequence of any of SEQ ID NO: 1-8, 16, 24-25, 29-40, 42, 50-51, 56 or 63;
　b) a polypeptide comprising an amino acid sequence having at least 85% sequence identity to the amino acid sequence of any of SEQ ID NO: 5 or 7;
　c) a polypeptide comprising an amino acid sequence having at least 90% sequence identity to the amino acid sequence of any of SEQ ID NO: 6, 8, 24, or 30;
　d) a polypeptide comprising an amino acid sequence having at least 95% sequence identity to the amino acid sequence of any of SEQ ID NO: 16, 25, 29, 31-34, 37, or 38; or
　e) a nucleotide sequence that encodes a polypeptide comprising an amino acid sequence having at least 98% sequence identity to the amino acid sequence of any of SEQ ID NO: 35, 36, 56 or 63, and
　heterologous amino acid sequences.

13. A composition comprising the polypeptide of claim 12.

14. The composition of claim 13, wherein said composition is selected from the group consisting of a powder, dust, pellet, granule, spray, emulsion, colloid, and solution.

15. The composition of claim 13, wherein said composition is prepared by desiccation, lyophilization, homogenization, extraction, filtration, centrifugation, sedimentation, or concentration of a culture of bacterial cells.

16. The composition of claim 13, comprising from about 1% to about 99% by weight of said polypeptide.

17. A method for controlling a hemipteran pest population, said method comprising contacting said population with a pesticidally-effective amount of the polypeptide of claim 12.

18. A method for killing a hemipteran pest, said method comprising contacting said pest with, or feeding to said pest, a pesticidally-effective amount of the polypeptide of claim 12.

19. A method for producing a polypeptide with pesticidal activity, said method comprising culturing the host cell of claim 6 under conditions in which the nucleic acid molecule encoding the polypeptide is expressed.

20. A plant or plant cell having stably incorporated into its genome a DNA construct comprising a nucleotide sequence that encodes a protein having pesticidal activity, wherein said nucleotide sequence is:
　a) the nucleotide sequence set forth in any of SEQ ID NO: 69-75, 83, 91, 92, 96-105, or 106;
　b) a nucleotide sequence that encodes a polypeptide comprising the amino acid sequence of any of SEQ ID NO: 1-8, 16, 24-25, 29-40, 42, 50-51, 56 or 63; or
　c) a nucleotide sequence that encodes a polypeptide comprising an amino acid sequence having at least 85% sequence identity to the amino acid sequence of any of SEQ ID NO: 5 or 7;
　d) a nucleotide sequence that encodes a polypeptide comprising an amino acid sequence having at least 90% sequence identity to the amino acid sequence of any of SEQ ID NO: 6, 8, 24, or 30;
　e) a nucleotide sequence that encodes a polypeptide comprising an amino acid sequence having at least 95% sequence identity to the amino acid sequence of any of SEQ ID NO: 16, 25, 29, 31-34, 37, or 38; or
　f) a nucleotide sequence that encodes a polypeptide comprising an amino acid sequence having at least 98% sequence identity to the amino acid sequence of any of SEQ ID NO: 35, 36, 56 or 63.

21. A method for increasing yield in a plant, said method comprising growing in a field a plant of or a seed thereof having stably incorporated into its genome a DNA construct comprising a nucleotide sequence that encodes a protein having pesticidal activity, wherein said nucleotide sequence is:
　a) the nucleotide sequence set forth in any of SEQ ID NO: 69-75, 83, 91, 92, 96-105, or 106;
　b) a nucleotide sequence that encodes a polypeptide comprising the amino acid sequence of any of SEQ ID NO: 1-8, 16, 24-25, 29-40, 42, 50-51, 56 or 63; or
　c) a nucleotide sequence that encodes a polypeptide comprising an amino acid sequence having at least 85% sequence identity to the amino acid sequence of any of SEQ ID NO: 5 or 7;
　d) a nucleotide sequence that encodes a polypeptide comprising an amino acid sequence having at least 90% sequence identity to the amino acid sequence of any of SEQ ID NO: 6, 8, 24, or 30;
　e) a nucleotide sequence that encodes a polypeptide comprising an amino acid sequence having at least 95% sequence identity to the amino acid sequence of any of SEQ ID NO: 16, 25, 29, 31-34, 37, or 38; or
　f) a nucleotide sequence that encodes a polypeptide comprising an amino acid sequence having at least 98% sequence identity to the amino acid sequence of any of SEQ ID NO: 35, 36, 56 or 63,
　wherein said field is infested with a pest against which said polypeptide has pesticidal activity.

22. A commodity product comprising the nucleic acid molecule of claim 1, wherein said product is whole or processed seeds or grain, animal feed, corn or soy meal, corn or soy flour, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans, soy yogurt, soy cheese, tofu, yuba, and cooked, polished, steamed, baked or parboiled grain.

23. The recombinant nucleic acid molecule of claim 1, wherein the nucleotide sequence encodes a polypeptide comprising an amino acid sequence having at least 90% sequence identity to the amino acid sequence of any of SEQ ID NO: 5-8, 24, or 30.

24. The recombinant nucleic acid molecule of claim 1, wherein the nucleotide sequence encodes a polypeptide comprising an amino acid sequence having at least 95% sequence identity to the amino acid sequence of any of SEQ ID NO: 5-8, 16, 24, 25, 29-34, 37, or 38.

25. The recombinant nucleic acid molecule of claim 1, wherein the nucleotide sequence encodes a polypeptide comprising an amino acid sequence having at least 99% sequence identity to the amino acid sequence of any of SEQ ID NO: 5-8, 16, 24, 25, 29-38, 56 or 63.

26. The recombinant nucleic acid molecule of claim 1, wherein the nucleotide sequence encodes the amino acid sequence of any of SEQ ID NO: 1-8, 16, 24-25, 29-40, 42, 50-51, 56 or 63.

27. The recombinant nucleic acid molecule of claim 1, wherein the nucleotide sequence encodes a polypeptide comprising the amino acid sequence of SEQ ID NO: 24.

28. The recombinant polypeptide of claim 12, wherein the polypeptide comprises an amino acid sequence having at least 90% sequence identity to the amino acid sequence of any of SEQ ID NO: 5-8, 24, or 30.

29. The recombinant polypeptide of claim 12, wherein the polypeptide comprises an amino acid sequence having at least 95% sequence identity to the amino acid sequence of any of SEQ ID NO: 5-8, 16, 24, 25, 29-34, 37, or 38.

30. The recombinant polypeptide of claim 12, wherein the polypeptide comprises an amino acid sequence having at least 99% sequence identity to the amino acid sequence of any of SEQ ID NO: 5-8, 16, 24, 25, 29-38, 56 or 63.

31. The recombinant polypeptide of claim 12, wherein the polypeptide comprises the amino acid sequence of any of SEQ ID NO: 1-8, 16, 24-25, 29-40, 42, 50-51, 56 or 63.

32. The recombinant polypeptide of claim 12, wherein the polypeptide comprises the amino acid sequence of SEQ ID NO: 24.

33. The method of claim 21, wherein the nucleotide sequence encodes a polypeptide comprising an amino acid sequence having at least 90% sequence identity to the amino acid sequence of any of SEQ ID NO: 5-8, 24, or 30.

34. The method of claim 21, wherein the nucleotide sequence encodes a polypeptide comprising an amino acid sequence having at least 95% sequence identity to the amino acid sequence of any of SEQ ID NO: 5-8, 16, 24, 25, 29-34, 37, or 38.

35. The method of claim 21, wherein the nucleotide sequence encodes a polypeptide comprising an amino acid sequence having at least 99% sequence identity to the amino acid sequence of any of SEQ ID NO: 5-8, 16, 24, 25, 29-38, 56 or 63.

36. The method of claim 21, wherein the nucleotide sequence encodes a polypeptide comprising the polypeptide comprises the amino acid sequence of any of SEQ ID NO: 1-8, 16, 24-25, 29-40, 42, 50-51, 56 or 63.

* * * * *